United States Patent
Bornzin et al.

(10) Patent No.: US 11,291,400 B2
(45) Date of Patent: Apr. 5, 2022

(54) METHOD AND SYSTEM FOR DETECTING LOW LEVEL P-WAVES

(71) Applicant: Pacesetter, Inc., Sylmar, CA (US)

(72) Inventors: Gene A. Bornzin, Santa Monica, CA (US); Chunlan Jiang, Northridge, CA (US); Jong Gill, Valencia, CA (US); Xiaoyi Min, Camarillo, CA (US); Kyungmoo Ryu, Palmdale, CA (US); Gabriel A. Mouchawar, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 101 days.

(21) Appl. No.: 16/871,261

(22) Filed: May 11, 2020

(65) Prior Publication Data

US 2021/0345900 A1 Nov. 11, 2021

(51) Int. Cl.
*A61B 5/00* (2006.01)
*A61B 5/35* (2021.01)
*A61B 5/339* (2021.01)
*A61B 5/352* (2021.01)

(52) U.S. Cl.
CPC ............ *A61B 5/35* (2021.01); *A61B 5/0006* (2013.01); *A61B 5/339* (2021.01); *A61B 5/352* (2021.01); *A61B 5/686* (2013.01)

(58) Field of Classification Search
CPC ........... A61B 5/35; A61B 5/346; A61B 5/349; A61B 5/353; A61B 5/36; A61B 5/361; A61B 5/363; A61B 5/352; A61B 5/339; A61B 5/0006; A61B 5/686
See application file for complete search history.

(56) References Cited

U.S. PATENT DOCUMENTS

2009/0240157 A1* 9/2009 Lian .................... A61B 5/7264
600/510
2020/0376282 A1* 12/2020 Bornzin .................. A61B 5/29

* cited by examiner

*Primary Examiner* — Scott M. Getzow
(74) *Attorney, Agent, or Firm* — The Small Patent Law Group LLC; Dean D. Small

(57) ABSTRACT

A computer implemented method and system to detect P-waves in cardiac activity is provided. The system includes memory to store specific executable instructions. One or more processors are configured to execute the specific executable instructions for obtaining far field cardiac activity (CA) signals for a series of beats, applying a P-wave template to at least one sub-segment of the CA signals to obtain an alignment indicator and calculating an amplitude dependence (AD) indicator based at least in part on the P-wave template and the at least one sub-segment. The system analyzes the alignment indicator based on a first criteria, compares the AD indicator with a second criteria, designates a candidate P-wave to be an actual P-wave based on the analyzing and comparing and records results of the designating.

20 Claims, 12 Drawing Sheets

METHOD AND SYSTEM FOR DETECTING LOW LEVEL P-WAVES

FIELD OF THE INVENTION

Embodiments herein relate generally to implantable medical devices, and more particularly to detection of low-level P-waves and discrimination of noise in cardiac activity signals.

BACKGROUND OF THE INVENTION

Physicians implant insertable cardiac monitors (ICMs) to detect various arrhythmias, such as associated with syncope, atrial fibrillation (AF) (e.g., before and after ablation), bradycardia, tachycardia and cryptogenic stroke. Electrophysiologist are interested in detecting AF and ultimately treating AF with ablation. Physicians often ablate a patient multiple times and utilize ICMs to obtain objective information regarding an impact of the ablation upon AF. Various algorithms have been proposed for detecting AF. Among others, AF detection algorithms have been proposed that utilize R-R interval variability and other interval dependent information to identify AF episodes. However, in some instances, conventional AF detection algorithms may under detect AF episodes or declare an AF episode when none is present, such as in connection with over sensing.

Heretofore, ICMs have not been able to reliably utilize P-wave detection as a mechanism for identifying arrhythmias. Among other challenges, P-waves captured with ICM electrodes are very small, on the order of 10 to 60 microvolts and are often "lost in the noise", while R-waves are typically hundreds of microvolts. In order to enhance the signal to noise (S/N) ratio, it has been proposed to use signal averaging of P-waves to improve discrimination. However, P-wave averaging requires several beats to enhance the S/N ratio. This is not a dramatic increase in S/N ratio because the S/N ratio goes with the square root of the number of elements in the ensemble.

Also, a leadless pacemaker intended for implant within a ventricle has also been proposed that utilizes correlation for tracking far-field P-waves that are detected by electrodes on the housing of the leadless pacemaker while implanted in the ventricle. Tracking P-waves make VDD pacing a possibility enabling maintenance of the atrial contribution to ventricular filling in patients with an intact sinus mechanism. The far-field P-waves, detected by the leadless pacemaker, have an amplitude in the order of between 20 and 60 uV.

An opportunity remains to improve the accuracy of implantable devices for sensing P-waves, discriminating noise, accurately identifying various arrhythmias (e.g., syncope, AF, bradycardia, tachycardia and cryptogenic stroke), generating accurate diagnostics and computing short/long term trends in physiological signals leading to actionable insights and predictions

SUMMARY

In accordance with embodiments herein, a system for detecting P-waves in cardiac activity is provided. The system includes memory to store specific executable instructions. One or more processors are configured to execute the specific executable instructions for obtaining far field cardiac activity (CA) signals for a series of beats, applying a P-wave template to at least one sub-segment of the CA signals to obtain an alignment indicator and calculating an amplitude dependence (AD) indicator based at least in part on the P-wave template and the at least one sub-segment. The system analyzes the alignment indicator based on a first criteria, compares the AD indicator with a second criteria, designates a candidate P-wave to be an actual P-wave based on the analyzing and comparing and records results of the designating.

Optionally, the one or more processors may further be configured to execute the specific executable instructions for identifying an R-wave COI from a beat in the series of beats. The processors may define the P-wave search window to overlay the sub-segment of the CA signals at a predetermined time prior to the R-wave COI for the beat, may collect the subsegment of the CA signals overlaid by the P-wave search window, repeating the identifying, defining and collecting to obtain on ensemble of subsegments for the series of beats. The processors may combine the ensemble of subsegments to form an ensemble average of the CA signals within the P-wave search window for the series of beats and may calculate a correlation of the ensemble average with the P-wave template to obtain the alignment indicator.

Optionally, the applying by the one or more processors may further comprise applying the P-wave template to sub-segments of the CA signals along a P-wave search window to obtain, as the alignment indicator, a temporal alignment (TA) indicator across the P-wave search window, and wherein the analyzing by the one or more processors further comprises analyzing the TA indicator based on the first criteria to identify the candidate P-wave. The TA indicator may represent a measure of how changes in the P-wave template are associated with changes in the corresponding subsegments of the CA signals and wherein the first criteria corresponds to a maximum for the TA indicator over the P-wave search window. The candidate P-wave may correspond to the subsegment of the CA signal for which the corresponding TA indicator has the maximum.

Optionally, the one or more processors may be configured to iteratively correlate the P-wave template to the sub-segments of the CA signals along the P-wave search window to obtain a correlation function across the P-wave search window as the temporal alignment indicator. The one or more processors may be configured to analyze the temporal alignment indicator by identify a peak in the correlation function and identify the candidate P-wave based on the peak in the correlation function. The one or more processors may be configured to calculate a covariance function based on the correlation function, the covariance function representing the AD indicator.

Optionally, the second criteria may represent a tolerance range that may be defined based on a peak of the P-wave template. The one or more processors may be configured to determine whether the covariance function is within the tolerance range. The one or more processors may be configured to apply the P-wave template to the segments of an ensemble of CA signals collected over multiple beats. The one or more processors may be configured to calculate a plurality of P-wave templates associated with different postures and utilize a select one of the P-wave templates based on a current posture of the patient when the CA signals are collected.

In accordance with embodiments herein, a computer implemented method is provided. The method is under control of one or more processors configured with specific executable instructions. The method obtains far field cardiac activity (CA) signals for a series of beats, applies a P-wave template to at least one sub-segment of the CA signals to obtain an alignment indicator and calculates an amplitude dependence (AD) indicator based at least in part on the P-wave template and the at least one sub-segment. The method analyze the alignment indicator based on a first criteria, compares the AD indicator with a second criteria, designates a candidate P-wave to be an actual P-wave based on the analyzing and comparing and records results of the designating.

Optionally, the method may identify an R-wave COI from a beat in the series of beats. The method may define the P-wave search window to overlay the sub-segment of the CA signals at a predetermined time prior to the R-wave COI for the beat and may collect the subsegment of the CA signals overlaid by the P-wave search window. The method may repeat the identifying, defining and collecting to obtain on ensemble of subsegments for the series of beats, combining the ensemble of subsegments to form an ensemble average of the CA signals within the P-wave search window for the series of beats. The method may calculate a correlation of the ensemble average with the P-wave template to obtain the alignment indicator.

Optionally, the applying may further comprise applying the P-wave template to sub-segments of the CA signals along a P-wave search window to obtain, as the alignment indicator, a temporal alignment (TA) indicator across the P-wave search window, and wherein the analyzing further comprises analyzing the TA indicator based on the first criteria to identify the candidate P-wave. The one or more processors may be configured to at least one of: i) perform the applying, calculating, analyzing and comparing in a parallel manner, or ii) perform the applying, calculating, analyzing and comparing in a serial manner.

Optionally, the applying may include iteratively correlating the P-wave template to the sub-segments of the CA signals along the P-wave search window to obtain a correlation function across the P-wave search window as the temporal alignment indicator. The analyzing the temporal alignment indicator based on the first criteria may include identifying a peak in the correlation function and identifying the candidate P-wave based on the peak in the correlation function.

Optionally, the CA signals may represent intracardiac electrograms (IEGM). The method may comprise calculating the P-wave template by displaying on a graphical user interface (GUI) IEGM signals and surface electrocardiogram (EKG) signals. The method may receive a user input from the GUI an input designating at least one of: 1) P-waves on the IEGM signals, 2) P-waves on surface EKG signals and P waves on the IEGM signals, or 3) P-waves on the surface EKG signals. The user input may designate select points corresponding to the P-waves and may identify the segment of the CA signals that includes the corresponding P-waves. The method may repeat the displaying, receiving and identifying to calculate a plurality of P-wave templates associated with different postures and utilizing a select one of the P-wave templates based on a current posture of the patient when the CA signals are collected. The method may calculate separate P-wave templates corresponding to a patient standing, the patient sitting, the patient lying on his/her back, and the patient lying on each side.

The obtaining the CA signals may comprise collecting the CA signals in real time by an implantable medical device in connection with an arrhythmia detection process. The arrhythmia detection processes may identify variability in RR intervals within the series of beats in the CA signals, declare an arrhythmia episode based on variability in the RR intervals and may store a segment of the CA signals for the series of beats in connection with the arrhythmia episode. The process may iteratively implement the applying, calculating, analyzing, comparing, and designating to determine whether actual P waves occur consistently throughout the series of beats and may validate or reject the arrhythmia episode based on the determination of whether the actual P waves occur consistently throughout the series of beats.

DETAILED DESCRIPTION

Figure 1:
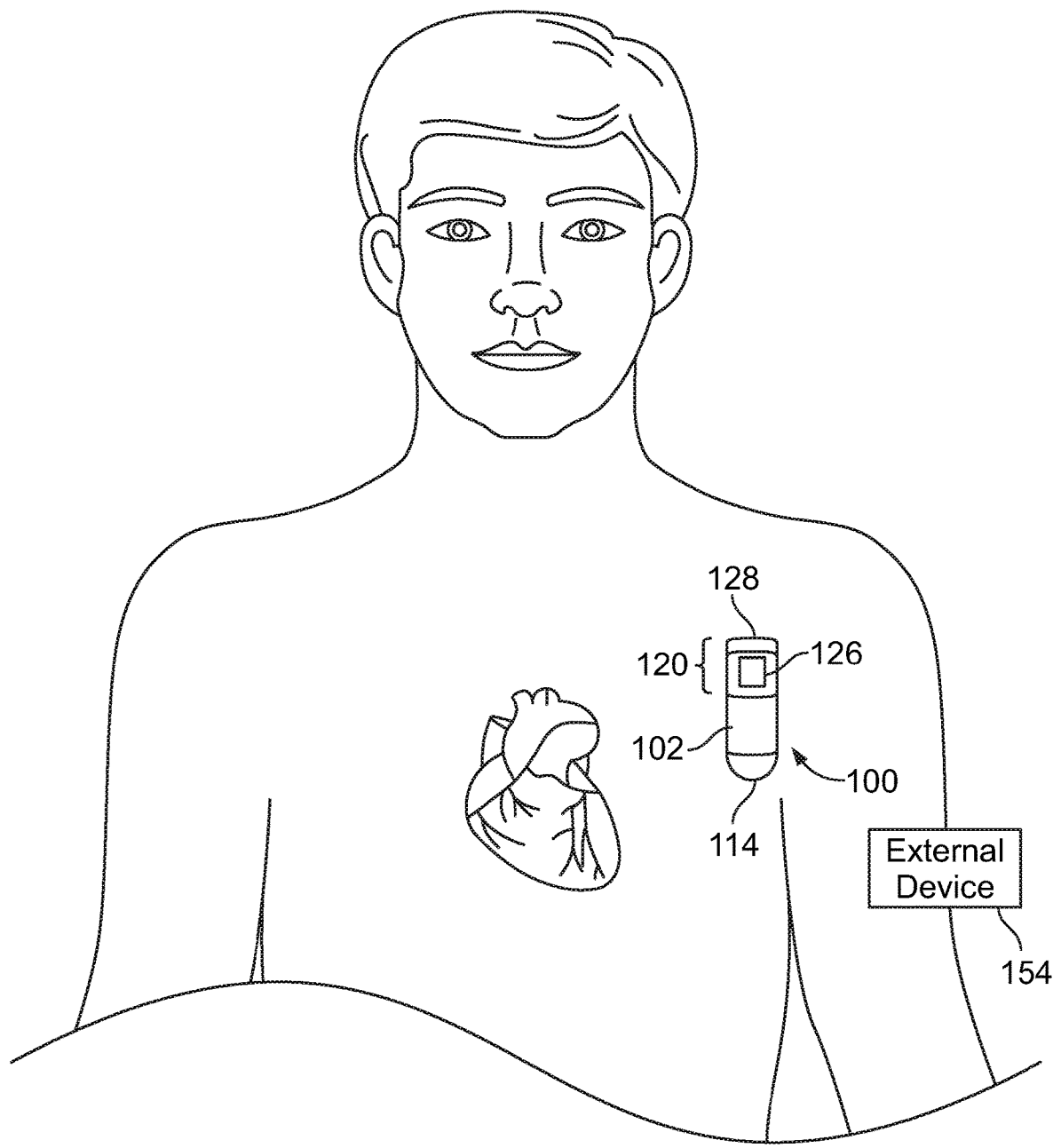
FIG. 1 illustrates an implantable cardiac monitoring device (ICM) intended for subcutaneous implantation at a site near the heart in accordance with embodiments herein.

The terms "cardiac activity signal", "cardiac activity signals", "CA signal" and "CA signals" (collectively "CA signals") are used interchangeably throughout to refer to an analog or digital electrical signal recorded by two or more electrodes positioned subcutaneous or cutaneous, where the electrical signals are indicative of cardiac electrical activity. The cardiac activity may be normal/healthy or abnormal/arrhythmic. Non-limiting examples of CA signals include ECG signals collected by cutaneous electrodes, and EGM signals collected by subcutaneous electrodes.

The terms "beat" and "cardiac event" are used interchangeably and refer to both normal or abnormal events.

The terms "normal" and "sinus" are used to refer to events, features, and characteristics of, or appropriate to, a heart's healthy or normal functioning.

The terms "abnormal," or "arrhythmic" are used to refer to events, features, and characteristics of, or appropriate to, an un-healthy or abnormal functioning of the heart.

The term "real-time" refers to a time frame contemporaneous with a normal or abnormal episode occurrences. For example, a real-time process or operation would occur during or immediately after (e.g., within minutes or seconds after) a cardiac event, a series of cardiac events, an arrhythmia episode, and the like.

In accordance with new and unique aspects herein, embodiments are proposed for detection far field P-waves. Among other things, the methods and systems herein: 1) detect an R-wave. 2) use an established P-wave template to correlate the template over an interval preceding the R-wave; and 3) determine whether two criteria are met to identify the presence of a P-wave when the template achieves what is deemed as a match, the methods and systems further determine whether and if the amplitude of the matching event is in accordance with the "typical" or projected amplitude of a P-wave.

Embodiments may be implemented in connection with one or more implantable medical devices (IMDs). Non-limiting examples of IMDs include one or more of implantable leadless monitoring and/or therapy devices, and/or alternative implantable medical devices. As a nonlimiting example, the IMD may include a transvenous lead located in a single chamber, such as in the right ventricle (e.g., a single chamber ICD), wherein far field P waves are measured and processed in accordance with embodiments herein. For example, the IMD may represent a cardiac monitoring device, pacemaker, cardioverter, cardiac rhythm management device, defibrillator, leadless monitoring device, leadless pacemaker and the like. For example, the IMD may include one or more structural and/or functional aspects of the device(s) described in U.S. Pat. No. 9,333,351 "Neurostimulation Method And System To Treat Apnea" and U.S. Pat. No. 9,044,610 "System And Methods For Providing A Distributed Virtual Stimulation Cathode For Use With An Implantable Neurostimulation System", which are hereby incorporated by reference.

Additionally or alternatively, the IMD may be a leadless implantable medical device (LIMD) that include one or more structural and/or functional aspects of the device(s) described in U.S. Pat. No. 9,216,285 "Leadless Implantable Medical Device Having Removable And Fixed Components" and U.S. Pat. No. 8,831,747 "Leadless Neurostimulation Device And Method Including The Same", which are hereby incorporated by reference. Additionally or alternatively, the IMD may include one or more structural and/or functional aspects of the device(s) described in U.S. Pat. No. 8,391,980 "Method And System For Identifying A Potential Lead Failure In An Implantable Medical Device" and U.S. Pat. No. 9,232,485 "System And Method For Selectively Communicating With An Implantable Medical Device", which are hereby incorporated by reference.

Additionally or alternatively, the IMD may be a subcutaneous IMD that includes one or more structural and/or functional aspects of the device(s) described in U.S. application Ser. No. 15/973,195, titled "Subcutaneous Implantation Medical Device With Multiple Parasternal-Anterior Electrodes" and filed May 7, 2018; U.S. application Ser. No. 15/973,219, titled "Implantable Medical Systems And Methods Including Pulse Generators And Leads" filed May 7, 2018; U.S. application Ser. No. 15/973,249, titled "Single Site Implantation Methods For Medical Devices Having Multiple Leads", filed May 7, 2018, which are hereby incorporated by reference in their entireties. Further, one or more combinations of IMDs may be utilized from the above incorporated patents and applications in accordance with embodiments herein.

Additionally or alternatively, the IMD may be a leadless cardiac monitor (ICM) that includes one or more structural and/or functional aspects of the device(s) described in U.S. patent application Ser. No. 15/084,373, filed Mar. 29, 2016, entitled, "METHOD AND SYSTEM TO DISCRIMINATE RHYTHM PATTERNS IN CARDIAC ACTIVITY," which is expressly incorporated herein by reference.

Additionally or alternatively, the IMD may implement the P-wave detection processes described herein, in connection the confirmation algorithms described in U.S. patent application Ser. No. 15/973,126, titled "METHOD AND SYSTEM FOR SECOND PASS CONFIRMATION OF DETECTED CARDIAC ARRHYTHMIC PATTERNS"; U.S. patent application Ser. No. 15/973,351, titled "METHOD AND SYSTEM TO DETECT R-WAVES IN CARDIAC ARRHYTHMIC PATTERNS"; U.S. patent application Ser. No. 15/973,307, titled "METHOD AND SYSTEM TO DETECT POST VENTRICULAR CONTRACTIONS IN CARDIAC ARRHYTHMIC PATTERNS"; and U.S. patent application Ser. No. 16/399,813, titled "METHOD AND SYSTEM TO DETECT NOISE IN CARDIAC ARRHYTHMIC PATTERNS."

All references, including publications, patent applications and patents, cited herein are hereby incorporated by reference to the same extent as if each reference were individually and specifically indicated to be incorporated by reference and were set forth in its entirety herein.

FIG. 1 illustrates an implantable cardiac monitoring device (ICM) 100 intended for subcutaneous implantation at a site near the heart. The ICM 100 includes a pair of spaced-apart sense electrodes 114, 126 positioned with respect to a housing 102. The sense electrodes 114, 126 provide for detection of far field electrogram signals. Numerous configurations of electrode arrangements are possible. For example, the electrode 114 may be located on a distal end of the ICM 100, while the electrode 126 is located on a proximal side of the ICM 100. Additionally or alternatively, electrodes 126 may be located on opposite sides of the ICM 100, opposite ends or elsewhere. The distal electrode 114 may be formed as part of the housing 102, for example, by coating all but a portion of the housing with a nonconductive material such that the uncoated portion forms the electrode 114. In this case, the electrode 126 may be electrically isolated from the housing 102 electrode by placing it on a component separate from the housing 102, such as the header 120. Optionally, the header 120 may be formed as an integral portion of the housing 102. The header 120 includes an antenna 128 and the electrode 126. The antenna 128 is configured to wirelessly communicate with an external device 154 in accordance with one or more predetermined wireless protocols (e.g., Bluetooth, Bluetooth low energy, Wi-Fi, etc.). The housing 102 includes various other components such as: sense electronics for receiving signals from the electrodes, a microprocessor for processing the signals in accordance with algorithms, such as the P-wave detection algorithm described herein, a loop memory for temporary storage of CA data, a device memory for long-term storage of CA signals upon certain triggering events, such as AF detection, sensors for detecting patient activity and a battery for powering components.

In at least some embodiments, the ICM 100 is configured to be placed subcutaneously utilizing a minimally invasive approach. Subcutaneous electrodes are provided on the housing 102 to simplify the implant procedure and eliminate a need for a transvenous lead system. The sensing electrodes may be located on opposite sides of the device and designed to provide robust episode detection through consistent contact at a sensor-tissue interface. The ICM 100 may be configured to be activated by the patient or automatically activated, in connection with recording subcutaneous ECG signals.

The ICM 100 senses far field, subcutaneous CA signals, processes the CA signals to detect arrhythmias and if an arrhythmia is detected, automatically records the CA signals in memory for subsequent transmission to an external device 154. The CA signal processing and arrhythmia detection is provided for, at least in part, by algorithms embodied in or implemented by the microprocessor. The ICM 100 includes one or more processors and memory that stores program instructions directing the processors to implement arrhythmia detection utilizing an on-board R-R interval irregularity (ORI) process that analyzes cardiac activity signals collected over one or more sensing channels.

Figure 2:
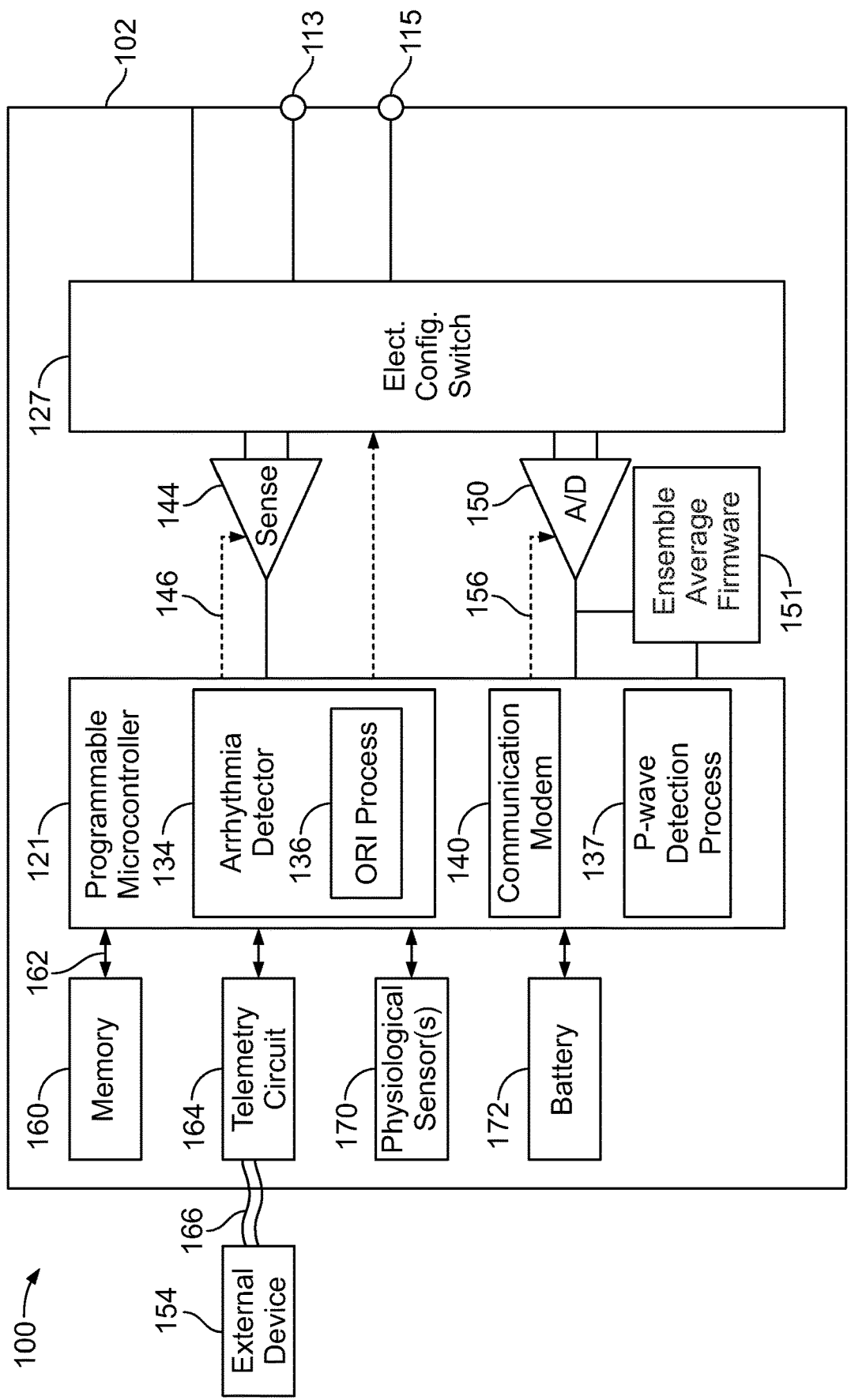
FIG. 2 shows a block diagram of the ICM formed in accordance with embodiments herein.

FIG. 2 shows a block diagram of the ICM 100 formed in accordance with embodiments herein. The ICM 100 may be implemented to monitor ventricular activity alone, or both ventricular and atrial activity through sensing circuit. The ICM 100 has a housing 102 to hold the electronic/computing components. The housing 102 (which is often referred to as the "can", "case", "encasing", or "case electrode") may be programmably selected to act as an electrode for certain sensing modes. Housing 102 further includes a connector (not shown) with at least one terminal 113 and optionally additional terminals 115. The terminals 113, 115 may be coupled to sensing electrodes that are provided upon or immediately adjacent the housing 102. Optionally, more than two terminals 113, 115 may be provided in order to support more than two sensing electrodes, such as for a bipolar sensing scheme that uses the housing 102 as a reference electrode. Additionally or alternatively, the terminals 113, 115 may be connected to one or more leads having one or more electrodes provided thereon, where the electrodes are located in various locations about the heart. The type and location of each electrode may vary.

The ICM 100 includes a programmable microcontroller 121 that controls various operations of the ICM 100, including cardiac monitoring. Microcontroller 121 includes a microprocessor (or equivalent control circuitry), RAM and/or ROM memory, logic and timing circuitry, state machine circuitry, and I/O circuitry. The microcontroller 121 also performs the operations described herein in connection with collecting cardiac activity data and analyzing the cardiac activity data to identify AF episodes.

A switch 127 is optionally provided to allow selection of different electrode configurations under the control of the microcontroller 121. The electrode configuration switch 127 may include multiple switches for connecting the desired electrodes to the appropriate I/O circuits, thereby facilitating electrode programmability. The switch 127 is controlled by a control signal from the microcontroller 121. Optionally, the switch 127 may be omitted and the I/O circuits directly connected to the housing electrode 114 and a second electrode 126. Microcontroller 121 includes an arrhythmia detector 134 that is configured to analyze cardiac activity signals to identify potential AF episodes as well as other arrhythmias (e.g., Tachcardias, Bradycardias, Asystole, etc.). By way of example, the arrhythmia detector 134 may implement an AF detection algorithm as described in U.S. Pat. No. 8,135,456, the complete subject matter of which is incorporated herein by reference. Although not shown, the microcontroller 121 may further include other dedicated circuitry and/or firmware/software components that assist in monitoring various conditions of the patient's heart and managing pacing therapies.

The ICM 100 is further equipped with a communication modem (modulator/demodulator) 140 to enable wireless communication. In one implementation, the communication modem 140 uses high frequency modulation, for example using RF, Bluetooth or Bluetooth Low Energy telemetry protocols. The signals are transmitted in a high frequency range and will travel through the body tissue in fluids without stimulating the heart or being felt by the patient. The communication modem 140 may be implemented in hardware as part of the microcontroller 121, or as software/firmware instructions programmed into and executed by the microcontroller 121. Alternatively, the modem 140 may reside separately from the microcontroller as a standalone component. The modem 140 facilitates data retrieval from a remote monitoring network. The modem 140 enables timely and accurate data transfer directly from the patient to an electronic device utilized by a physician.

The ICM 100 includes sensing circuit 144 selectively coupled to one or more electrodes that perform sensing operations, through the switch 127 to detect cardiac activity data indicative of cardiac activity. The sensing circuit 144 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the features of interest. In one embodiment, switch 127 may be used to determine the sensing polarity of the cardiac signal by selectively closing the appropriate switches.

The output of the sensing circuit 144 is connected to the microcontroller 121 which, in turn, determines when to store the cardiac activity data of CA signals (digitized by the A/D data acquisition system 150) in the memory 160. For example, the microcontroller 121 may only store the cardiac activity data (from the ND data acquisition system 150) in the memory 160 when a potential AF episode is detected. The sensing circuit 144 receives a control signal 146 from the microcontroller 121 for purposes of controlling the gain, threshold, polarization charge removal circuitry (not shown), and the timing of any blocking circuitry (not shown) coupled to the inputs of the sensing circuit.

In the example, a single sensing circuit 144 is illustrated. Optionally, the ICM 100 may include multiple sensing circuits, similar to sensing circuit 144, where each sensing circuit is coupled to two or more electrodes and controlled by the microcontroller 121 to sense electrical activity detected at the corresponding two or more electrodes. The sensing circuit 144 may operate in a unipolar sensing configuration or in a bipolar sensing configuration. Optionally, the sensing circuit 144 may be removed entirely and the microcontroller 121 perform the operations described herein based upon the CA signals from the ND data acquisition system 150 directly coupled to the electrodes.

The arrhythmia detector 134 of the microcontroller 121 includes an on-board R-R interval irregularity (ORI) process 136 that detects AF episodes using R-R interval irregularities as discussed in connection with FIGS. 17-18. The ORI process 136 may be implemented by firmware, software and/or circuits. The ORI process 136 uses a hidden Markov Chains and Euclidian distance calculations of similarity to assess the transitionary behavior of one R-wave (RR) interval to another and compare the patient's RR interval transitions to the known RR interval transitions during AF and non-AF episodes obtained from the same patient and/or many patients. The ORI process 136 detects AF episodes over a short number of RR intervals. For example, the ORI process 136 may implement the AF detection methods described in U.S. Pat. No. 8,135,456, the complete subject matter of which is incorporated herein by reference in its entirety.

The ICM 100 further includes an analog-to-digital ND data acquisition system (DAS) 150 coupled to one or more electrodes via the switch 127 to sample cardiac activity signals across any pair of desired electrodes. The data acquisition system 150 is configured to acquire cardiac electrogram (EGM) signals as CA signals, convert the raw analog data into digital data, and store the digital data as CA data for later processing and/or telemetric transmission to an external device 154 (e.g., a programmer, local transceiver, or a diagnostic system analyzer). The data acquisition system 150 is controlled by a control signal 156 from the microcontroller 121. The EGM signals may be utilized as the cardiac activity data that is analyzed for potential P-waves and episodes.

Figure 8:
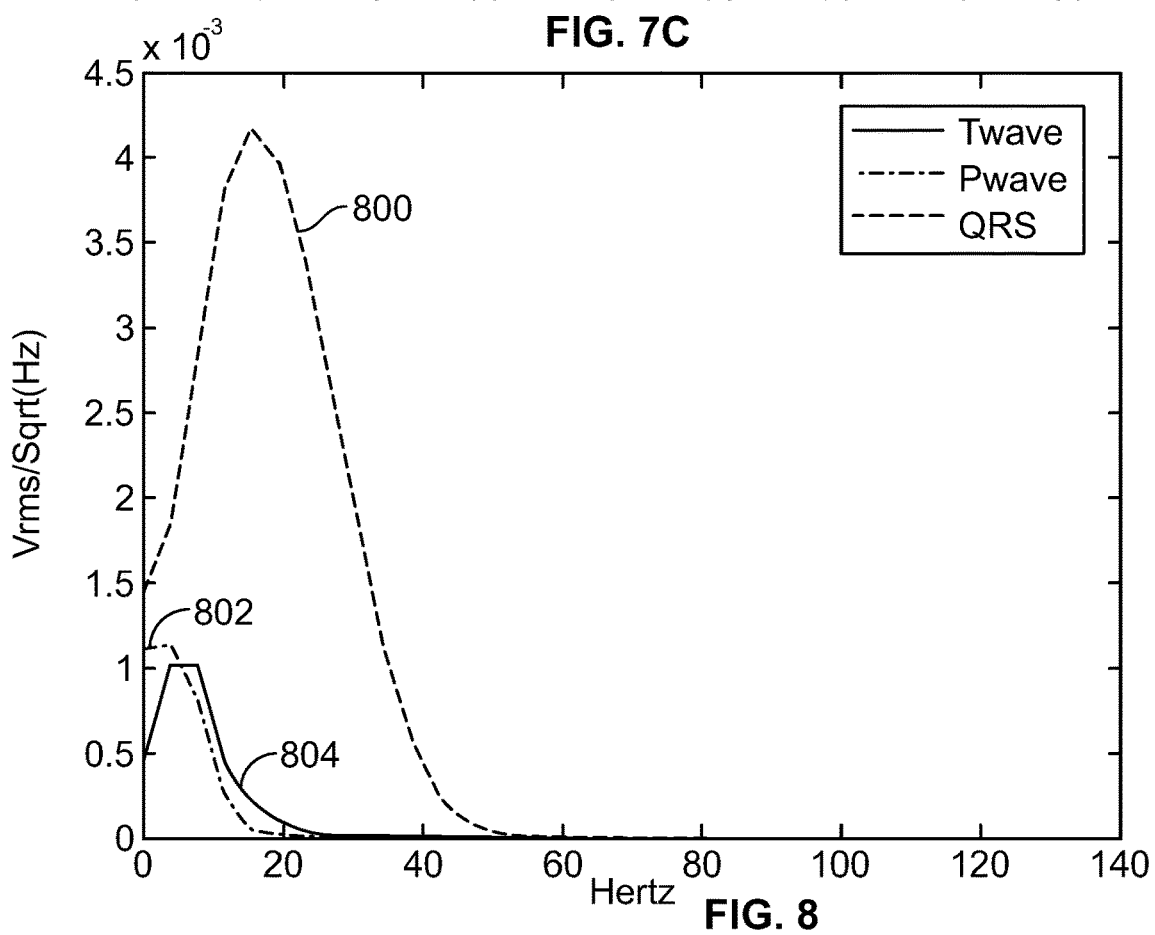
FIG. 8 illustrates a power spectra of CA signals collected by an ICM with the horizontal axis denoting frequency components of the CA signals and the vertical axis denoting power in accordance with embodiments herein.

FIG. 8 illustrates a power spectra of CA signals collected by an ICM with the horizontal axis denoting frequency components of the CA signals and the vertical axis denoting power (Vrms/Sqrt(Hz)). A first trace 800 represents the power spectrum of an R-wave. A second trace 804 represents the power spectrum of a T-wave. A third trace 802 represents the power spectrum of a P-wave. Note that the P-wave has very little energy above 16 Hertz, whereas the R-wave has very little energy above 40 Hz. A basic fundamental peak in the power spectra of a P-wave is at around 3 to 4 Hertz, whereas the peak in the power spectrum of an R-wave is between 20 Hz and 30 Hz.

In accordance with new and unique aspects herein, it has been recognized that a sampling rate appropriate for R-wave detection and analysis is much higher than a sampling rate necessary for P-wave detection and analysis. The Nyquist sampling theorem provides that a band limited continuous time signal can be sampled and substantially completely reconstructed from samples if the waveform is sampled over twice as fast as the highest frequency component of the waveform being sampled. In the foregoing examples, the R-wave has very little energy in the frequency components above 40 Hz (corresponding to a Nyquist frequency at or above hundred Hz), whereas a P-wave has very little energy in the frequency components above 16 Hertz (corresponding to a Nyquist limit at or above 40 Hz).

For example, in connection with R-wave detection and analysis, the data acquisition system 150 may collect a new data sample from the CA signal approximately every 2 ms (corresponding to a sampling rate of 512 Hz). The data samples may then all be stored (every 2 ms). Alternatively, only a subset of the data samples may be stored. Additionally or alternatively, the data samples may be combined into ensemble averages and then stored. For example, the data sample from the CA signals may be stored approximately every 8 ms (corresponding to a storage rate of approximately 128 Hz), such as storing every fourth data sample or storing an ensemble average of every four data samples. In R-wave typically exhibits a sharper and narrower peak as compared to the peak and shape of a P-wave. The foregoing example of data sampling rates affords a desired sampling rate to achieve a desired level of accuracy when detecting and analyzing R waves.

However, given the different power spectrums (and peak shapes) of an R-wave and a P-wave, it has been recognized that a lower sampling rate may be utilized in connection with P-wave detection without sacrificing any accuracy. For example, in accordance with embodiments herein, it has been found that sampling at 64 samples per second would more than exceed the Nyquist Frequency (around 40 Hz). Consequently, it would only require approximately 24 samples of the CA signals spread over a 400 ms P-wave search window to accurately capture a P-wave. In accordance with embodiments herein, methods and systems could easily determine the peak of the P-wave from the peak correlation with the template based on a sampling rate of 1 digitized CA signal data sample every 15 ms. Sampling 100 ms on either side of the anticipated peak of the P-wave would only require 13 samples to capture the P-wave. For example, if the peak correlation with the P-wave template occurs at 120 ms prior to the R-wave, then sampling from 220 ms to 20 ms prior to the R-wave should provide an adequate P-wave detection window.

The A/D DAS 150 samples the CA signals at a rate based on the characteristic of interest (COI) in the CA signals. In many implantable devices, it is desirable to sample the CA signals over at least one channel at a sampling rate sufficient to capture COI from the R-wave, and thus the CA signals may be sampled at around 512 Hz (and optionally saved at a rate of 128 Hz). In R-wave detection and analysis channel or processing path may then analyze the data samples (collected over the higher rate of 512 or 128) for R-wave characteristics of interest. However, a P-wave detection process may only obtain a subset of the data samples (collected over the higher data sample collection channel). The subset of data samples may be collected through decimation or other processes. For example, P-wave detection process may pull a subset of the data samples for processing, such as every eight data sample from the 512 Hz sampling rate. In the foregoing example, a single channel is used for analog to digital conversion and filtering, with the resulting digitized/filtered data passed along alternative channels, namely in R-wave processing channel at a higher data rate and a P-wave processing channel at a lower data rate. Additionally or alternatively, separate analog-to-digital conversion and filtering channels may be provided, such as when different filtering requirements are of interest (e.g., different pass bands, different bandwidths and the like). When separate channels are utilized, the first or primary A/D channel may be utilized to collect data samples in connection with R-wave detection at the higher 512 Hz data sampling rate, while a second or secondary A/D channel is utilized to collect data samples in connection with P-wave detection at the lower 64 Hz data sampling rate.

A limited number of digitized data samples may be collected from each individual CA signal segment and then added to the ensemble average. Embodiments herein utilize very few data samples (e.g., as few as four samples per P-wave search window) or as many more samples as appropriate to achieve a desired S/N ratio or frequency of P-wave verification. The number of digitized data samples per CA signal segment may be relatively limited because, among other things, P-waves have relatively low frequency content below 20 Hz. Therefore, sampling at 64 samples per second should provide adequate capture of the P-wave. Furthermore, as the algorithm predicts the expected occurrence of the P-wave peak relative to the R-wave, then sampling 100 ms on either side of the peak provides a window that captures the entire P-wave. Averaging is achieved with as few as 13 samples added to the ensemble average per cardiac cycle.

The digital CA data samples are passed to the microcontroller 121 and to ensemble averaging (EA) firmware 151. The EA firmware 151 is configures to collect and combine segments of CA data samples from multiple beats, within corresponding P-wave search windows. For example, the EA firmware 151 may average together CA data samples from 3-16 beats. As a further example, the A/D converter 150 may sample the analog CA signals at a higher sampling rate associated with detection and analysis of R-wave characteristics of interest (e.g., one data sample every 2 ms or a sampling rate of approximately 512 Hz). The EA firmware 151 may only pull/obtain (e.g., through decimation) a subset of the data samples output from the A/D converter 150 at a lower sampling rate (e.g., one data sample every 16 ms or a data sampling rate of approximately 64 Hz).

Optionally, a first A/D DAS may be used to collect P-wave segments at a first sampling rate and a second A/D DAS may be used to collect the entire CA signal and/or R-wave segments at a second higher sampling rate.

The microcontroller 121 also includes a P-wave detection process 137 that may be implemented by one or more processors that are configured to execute the specific executable instructions stored in memory. The A/D converter 150, under control of the microcontroller 121, obtains far field cardiac activity (CA) signals for a series of beats. The P-wave detection process 137 applies a P-wave template to at least one subsegment of the CA signals to obtain an alignment indicator. In accordance with the embodiment of FIG. 3A, the P-wave detection process 137 applies a P-wave template to sub-segments of the CA signals along the P-wave search window to obtain a temporal alignment (TA) indicator, as the alignment indicator, across the P-wave search window. Additionally or alternatively, in accordance with the embodiment of FIG. 3B, the P-wave detection process 137 identifies an R-wave COI from a beat in the series of beats, defines the P-wave search window to overlay the sub-segment of the CA signals at a predetermined time prior to the R-wave COI for the beat, and collects the subsegment of the CA signals overlaid by the P-wave search window. The P-wave detection process 137 repeats the identifying, defining and collecting operations to obtain on ensemble of subsegments for the series of beats. The P-wave detection process 137 combines the ensemble of subsegments to form an ensemble average of the CA signals within the P-wave search window for the series of beats and calculates a correlation of the ensemble average with the P-wave template to obtain the alignment indicator.

Figure 3A:
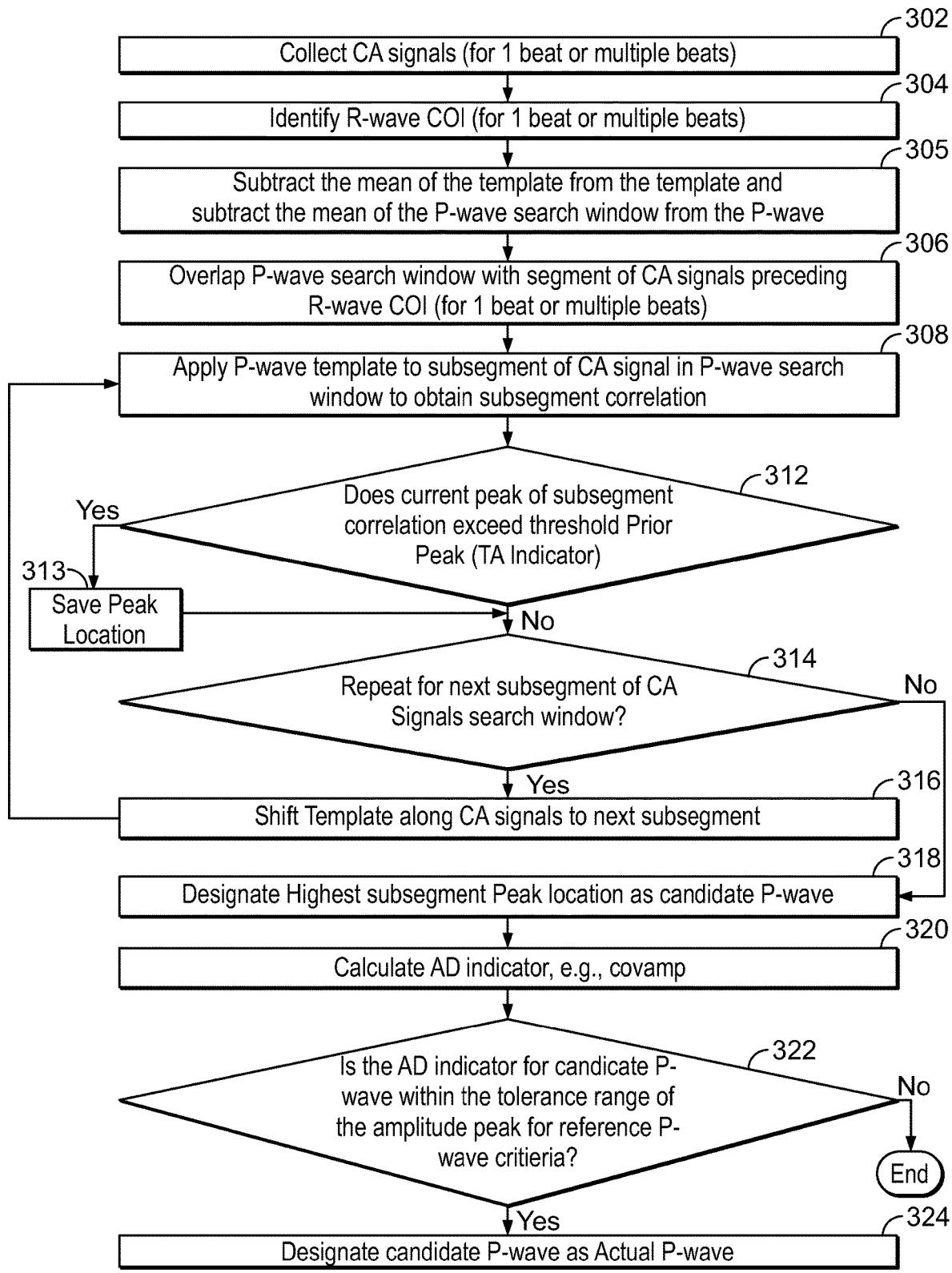
FIG. 3A shows a process for detecting P-waves in accordance with embodiments herein.

The P-wave detection process 137 also calculates an amplitude dependence (AD) indicator based at least in part on the P-wave template and at least one of the subsegment in connection with the embodiment of FIG. 3A, the 80 indicator is calculated based on the TA indicator. The P-wave detection process 137 analyzes the alignment indicator based on a first criteria to identify a candidate P-wave. The P-wave detection process 137 compares the AD indicator with a second criteria. The P-wave detection process 137 designates the candidate P-wave to be an actual P-wave based on the first and second comparing, and records results of the designating.

As explained herein, the first criteria may correspond to a maximum for the TA indicator over the P-wave search window, the candidate P-wave corresponding to the subsegment of the CA signal for which the corresponding TA indicator has the maximum. Additionally or alternatively, the P-wave detection process 137 utilizes the one or more processors to at least one of: i) perform the applying, calculating, analyzing and comparing in a parallel manner, or ii) perform the applying, calculating, analyzing and comparing in a serial manner. Additionally or alternatively, the P-wave detection process 137 is configured to iteratively correlate the P-wave template to the sub-segments of the CA signals along the P-wave search window to obtain a correlation function across the P-wave search window as the temporal alignment indicator. Additionally or alternatively, the P-wave detection process 137 is configured to analyze the temporal alignment indicator by identify a peak in the correlation function and identify the candidate P-wave based on the peak in the correlation function. Additionally or alternatively, the P-wave detection process 137 is configured to calculate a covariance function based on the correlation function, the covariance function representing the AD indicator. As explained herein, the second criteria may represent a tolerance range that is defined based on a peak of the P-wave template, and wherein the one or more processors are configured to determine whether the covariance function is within the tolerance range. Additionally or alternatively, the P-wave detection process 137 is configured to apply the P-wave template to the segments of an ensemble of CA signals collected over multiple beats. Additionally or alternatively, the P-wave detection process 137 is configured to calculate a plurality of P-wave templates associated with different postures and utilize a select one of the P-wave templates based on a current posture of the patient when the CA signals are collected.

By way of example, the external device 154 may represent a bedside monitor installed in a patient's home and utilized to communicate with the ICM 100 while the patient is at home, in bed or asleep. The external device 154 may be a programmer used in the clinic to interrogate the ICM 100, retrieve data and program detection criteria and other features. The external device 154 may be a handheld device (e.g., smartphone, tablet device, laptop computer, smartwatch and the like) that can be coupled over a network (e.g., the Internet) to a remote monitoring service, medical network and the like. The external device 154 facilitates access by physicians to patient data as well as permitting the physician to review real-time CA signals while collected by the ICM 100.

The microcontroller 121 is coupled to a memory 160 by a suitable data/address bus 162. The programmable operating parameters used by the microcontroller 121 are stored in memory 160 and used to customize the operation of the ICM 100 to suit the needs of a particular patient. Such operating parameters define, for example, detection rate thresholds, sensitivity, automatic features, AF detection criteria, activity sensing or other physiological sensors, and electrode polarity, etc.

In addition, the memory 160 stores the cardiac activity data, as well as the markers and other data content associated with detection of arrhythmia episodes. The operating parameters of the ICM 100 may be non-invasively programmed into the memory 160 through a telemetry circuit 164 in telemetric communication via communication link 166 with the external device 154. The telemetry circuit 164 allows intracardiac electrograms and status information relating to the operation of the ICM 100 (as contained in the microcontroller 121 or memory 160) to be sent to the external device 154 through the established communication link 166. In accordance with embodiments herein, the telemetry circuit 164 conveys the cardiac activity data, markers and other information related to AF episodes.

The ICM 100 may further include magnet detection circuitry (not shown), coupled to the microcontroller 121, to detect when a magnet is placed over the unit. A magnet may be used by a clinician to perform various test functions of the housing 102 and/or to signal the microcontroller 121 that the external device 154 is in place to receive or transmit data to the microcontroller 121 through the telemetry circuits 164.

The ICM 100 can further include one or more physiologic sensors 170. Such sensors are commonly referred to (in the pacemaker arts) as "rate-responsive" or "exercise" sensors. The physiological sensor 170 may further be used to detect changes in the physiological condition of the heart, or diurnal changes in activity (e.g., detecting sleep and wake states). Signals generated by the physiological sensors 170 are passed to the microcontroller 121 for analysis and optional storage in the memory 160 in connection with the cardiac activity data, markers, episode information and the like. While shown as being included within the housing 102, the physiologic sensor(s) 170 may be external to the housing 102, yet still be implanted within or carried by the patient. Examples of physiologic sensors might include sensors that, for example, activity, temperature, sense respiration rate, pH of blood, ventricular gradient, activity, heart sounds, position/posture, minute ventilation (MV), and so forth.

A battery 172 provides operating power to all of the components in the ICM 100. The battery 172 is capable of operating at low current drains for long periods of time. The battery 172 also desirably has a predictable discharge characteristic so that elective replacement time can be detected. As one example, the housing 102 employs lithium/silver vanadium oxide batteries. The battery 172 may afford various periods of longevity (e.g., three years or more of device monitoring). In alternate embodiments, the battery 172 could be rechargeable. See for example, U.S. Pat. No. 7,294,108, Cardiac event micro-recorder and method for implanting same, which is hereby incorporated by reference.

The ICM 100 provides a simple to configure data storage option to enable physicians to prioritize data based on individual patient conditions, to capture significant events and reduce risk that unexpected events are missed. The ICM 100 may be programmable for pre- and post-trigger event storage. For example, the ICM 100 may be automatically activated to store 10-120 seconds of CA data prior to an event of interest and/or to store 10-120 seconds of post CA data. Optionally, the ICM 100 may afford patient triggered activation in which pre-event CA data is stored, as well as post event CA data (e.g., pre-event storage of 1-15 minutes and post-event storage of 1-15 minutes). Optionally, the ICM 100 may afford manual (patient triggered) or automatic activation for CA data. Optionally, the ICM 100 may afford additional programming options (e.g., asystole duration, bradycardia rate, tachycardia rate, tachycardia cycle count). The amount of CA data storage may vary based upon the size of the memory 160.

The ICM 100 may provide comprehensive safe diagnostic data reports including a summary of heart rate, in order to assist physicians in diagnosis and treatment of patient conditions. By way of example, reports may include episode-related diagnostics for auto trigger events, episode duration, episode count, episode date/time stamp and heart rate histograms. The ICM 100 may be configured to be relatively small (e.g., between 2-10 cc in volume) which may, among other things, reduce risk of infection during implant procedure, afford the use of a small incision, afford the use of a smaller subcutaneous pocket and the like. The small footprint may also reduce implant time and introduce less change in body image for patients.

FIG. 3A shows a process for detecting P-waves in accordance with embodiments herein. By way of example, the operations of FIG. 3A may be implemented, as part of an initial arrhythmia detection process and/or a confirmatory process (e.g., where cardiac activity signals have been previously analyzed by an AF detection module). The process may continuously implement the P-wave detection process and/or initiate the operations of FIG. 3A attempting to verify whether one or more episodes in a CA data set, are in fact an arrhythmia episode or a normal rhythmic/sinus episode. Optionally, the operations of FIG. 3A may be implemented in connection with a CA data set that has not been previously analyzed for potential AF episodes. In the primary embodiment described herein, the operations of FIG. 3A are implemented by the processor, firmware and other circuitry within the ICM. Additionally or alternatively, the operations of FIG. 3A may be implemented as part of a local or distributed system. For example, the sensing operations may be performed by the ICM, with the CA data transmitted to a local external device and/or a remote server, which performs the additional operations described herein. Additionally or alternatively, a larger portion of the operations may be implemented by the ICM (e.g., correlation, calculation, and designation of actual P-waves), while a smaller portion (e.g., generation of templates, setting criteria) of the operations are implemented by the local external device and/or remote server. The analysis of FIG. 3A may be implemented as infrequently as once a day or every few hours.

In accordance with new and unique aspects herein, a P-wave detection process is described that utilizes two criteria for positive identification of an actual P-wave. The first criteria relate to correlation, while the second criteria relate to a determination of whether a P-wave amplitude is within a projected range (e.g., covariance amplitude at a correlation peak is within a tolerance range of a maximum covariance amplitude).

At 302, CA signals are collected over one or more sensing vectors. For example, the CA signals may be collected over a sensing vector defined between a combination of electrodes provided on the housing of the ICM or leadless device, where the sensing vector represents a far field sensing vector as the ICM or leadless device is implanted remote from an atrium of the heart.

At 304, one or more processors analyze the CA signals to identify an R-wave characteristic of interest (COI). For example, the R-wave COI may represent a peak of the R-wave or some other characteristic of the morphology of the R-wave. As one nonlimiting example, the R-wave COI may be identified utilizing the methods and systems described in co-pending application entitled "METHOD AND SYSTEM TO DETECT R-WAVES IN CARDIAC ACTIVITY SIGNALS" (filed Jun. 13, 2018 Ser. No. 16/007,878), the complete subject matter which is expressly incorporated herein by reference in its entirety.

At 305, the one or more processors subtract a mean for the template from the subsegment correlation values. The subtraction operation at 305 may optionally be performed or omitted. When the subtraction is performed, the process subtracts the 1) mean of the template and 2) CA signals correlated with the template, so that $x_i$ and $y_i$ are rendered zero mean functions.

At 306, the one or more processors apply a P-wave template to at least one subsegment of the CA signals. For example, the one or more processors overlap a P-wave search window onto a segment of the CA signals. The P-wave search window is longer than the P-wave template and thus, the segment of CA signals overlaid by the P-wave search window includes multiple sub segments having a length corresponding to the P-wave template. The P-wave search window is aligned at a desired point in time that precedes the R-wave. For example, the P-wave search window may be positioned to begin approximately 350 ms prior to the peak of the R-wave. As another nonlimiting example, the P-wave search window may be positioned to precede the R-wave such that the search window is generally centered at a point in time between 70 to 200 ms prior to the peak of the R-wave. The width of the P-wave search window may be varied, such as beginning 30 ms before an expected location of the P-wave and continuing 30 ms after the expected location of the P-wave. A longer or shorter window may be defined.

In the foregoing manner, the processors utilize the R-wave peak to learn where the P-wave is expected to occur. As explained herein, the search for the actual P-wave analyzes subsegments of the P-wave search window beginning some desired interval before, and continuing a desired interval after, the point in time corresponding to the expected location of the P-wave. By positioning a P-wave search window in the foregoing manner, in accordance with aspects herein, computational burden is reduced and computational deficiency is improved by finding the R-wave and then searching subsegments along the limited duration of the search window for the P-wave, as opposed to all or a larger portion of the CA signals.

Optionally, the identifying operation at 304 may be omitted entirely and the P-wave search window may be applied continuously across an entire duration of the CA signals, without limit to a particular time region preceding an R-wave. In this alternative embodiment, the process may continuously search for P-waves. When a P-wave is identified, the P-wave marker may be recorded at the corresponding point in time along the CA signals. Separately, R-waves may be identified, and R-wave markers stored with the CA signals to show P-wave and R-wave dis-association, such as consistent with complete heart block, AF and other arrhythmias.

Additionally or alternatively, the operations at 302-306 may be repeated to form an ensemble of CA signals from multiple beats that fall within corresponding P-wave search windows. When a P-wave is exceedingly small, it becomes more difficult to detect some of the P-waves, because the P-wave is lost in noise. In accordance with new and unique aspects herein, this problem is at least partially overcome by increasing the signal-to-noise (S/N) ratio by ensemble averaging the P-wave without unduly increasing processing complexity. If the noise is truly random and uncorrelated, the average of the noise will approach zero. Ensemble averaging increases the S/N ratio by the square root of the number of elements in the ensemble as shown in equation 3.

$$\left(\frac{S}{N}\right)_n = \sqrt{n}\left(\frac{S}{N}\right)_i \qquad \text{Equation 3)}$$

For example, if an algorithm averages P-waves of 11-microvolt amplitude in a 16-element ensemble, the signal averaged P-wave has effectively the same signal quality possessed by 40-microvolt P-wave. The process for signal averaging is to first identify a R-wave and then to retrospectively average the elements in a window (e.g., 300 to 400 ms window prior to the R-wave. Next the process compares the ensemble averaged P-wave, to a signal averaged P-wave template using the correlation and amplitude criteria calculated using equation 1) and 2). A high-quality template can be acquired by an operator using an algorithm that performs ensemble averaging (e.g., 16 or more P-waves). The process applies the methods of adaptive templates to different postures and heart rates and re-establishes the template(s) by continuously updating the template(s) automatically as described above.

Utilizing ensemble averaged P-waves is relatively computationally efficient. For each R-wave, an algorithm adds the preceding P-wave to a running average P-wave. This may require as few as 13 additions per cardiac cycle. This is a relatively modest demand on the processor.

In accordance with new and unique aspects herein, it has been recognized that a P-wave ensemble may be constructed utilizing a relatively small number of digitized data samples. A limited number of digitized data samples may be collected from each individual CA signal segment and then added to the ensemble average. Embodiments herein utilize very few data samples (e.g., as few as four samples per P-wave search window) or as many more samples as appropriate to achieve a desired S/N ratio or frequency of P-wave verification. The number of digitized data samples per CA signal segment may be relatively limited because, among other things, P-waves have relatively low frequency content below 20 Hz. Therefore, sampling at 64 samples per second should provide adequate capture of the P-wave. Furthermore, as the algorithm predicts the expected occurrence of the P-wave peak relative to the R-wave, then sampling 100 ms on either side of the peak provides a window that captures the entire P-wave. Averaging is achieved with as few as 13 samples added to the ensemble average per cardiac cycle.

Optionally, the ensemble averaging may be implemented in hardware, such as through one or more averaging registers that are utilized to collect corresponding CA data samples (e.g., 4-20) for one cardiac beat and combine the CA data samples from an ensemble of cardiac beats, without utilizing a processor and software to implement the averaging. When implemented in hardware, a software algorithm implementer need not be set up.

Figure 5:
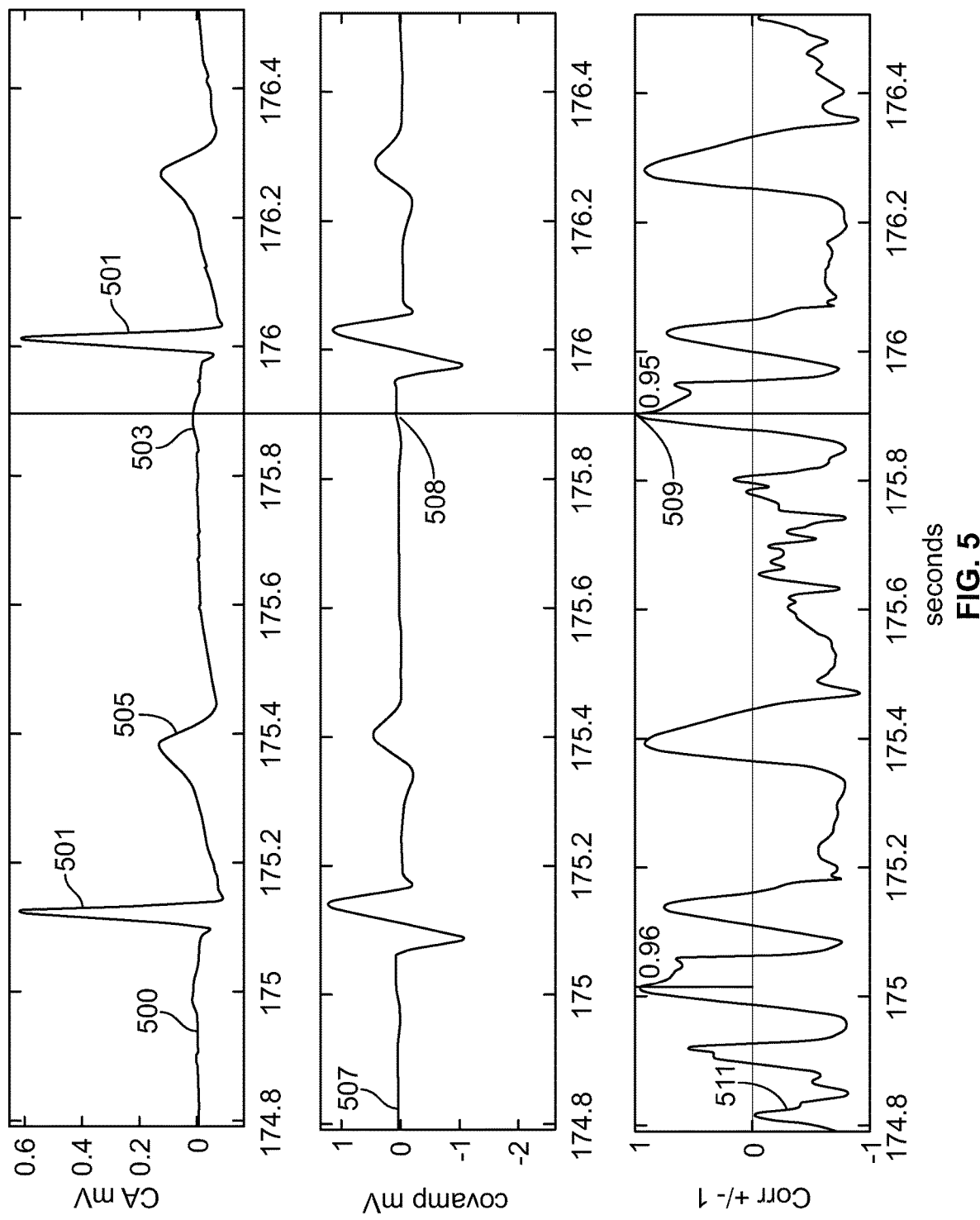
FIG. 5 illustrates a first example of a CA signal, correlation function and covariance function determined in accordance with embodiments herein.
Figure 6:
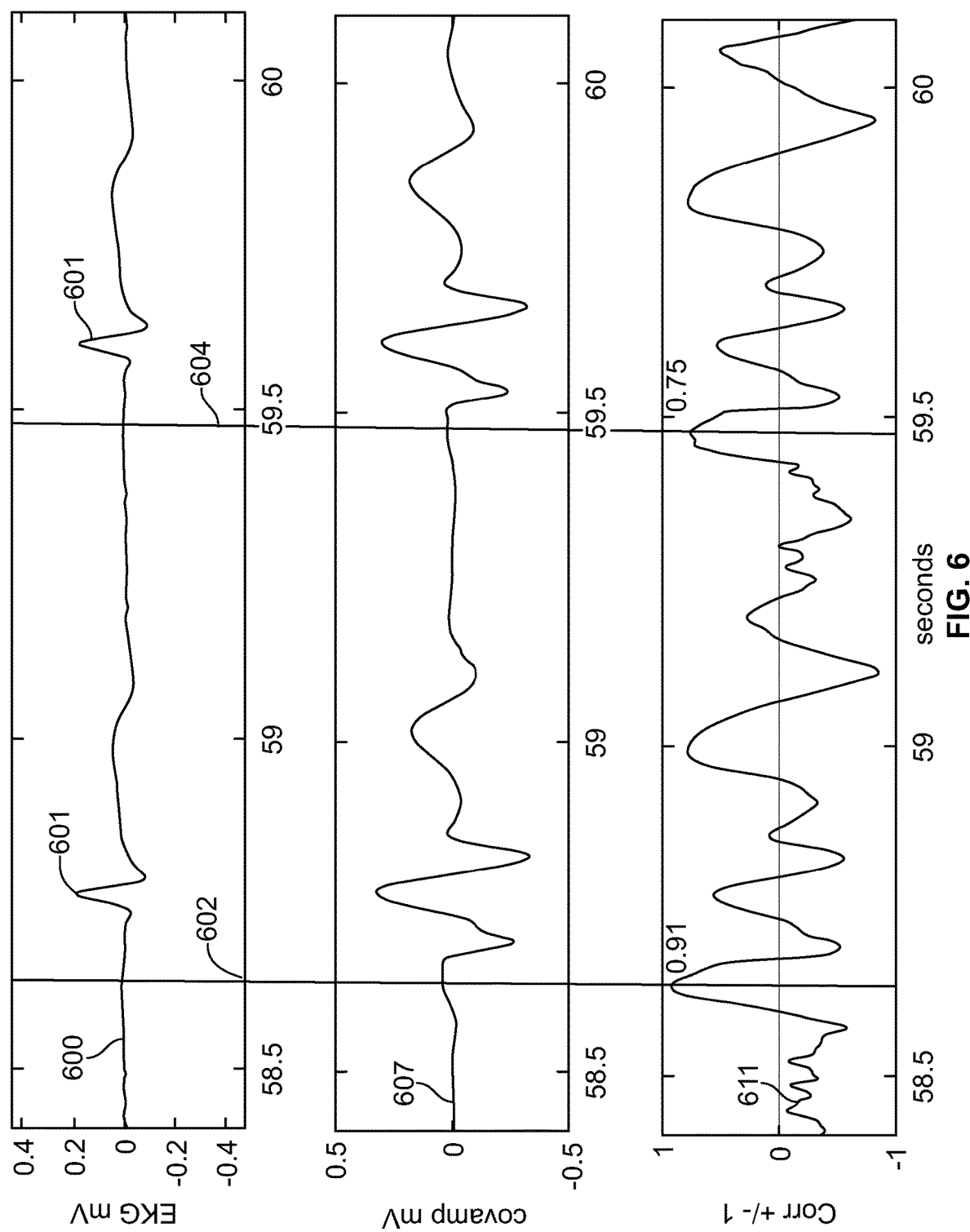
FIG. 6 illustrates a second example of a CA signal, correlation function and covariance function determined in accordance with embodiments herein.

At 308, the one or more processors apply the P-wave template to at least one subsegment of the CA signals to obtain an alignment indicator. In the embodiment of FIG. 3A, the one or more processors apply a P-wave template to sub-segments of the CA signals along the P-wave search window to obtain a temporal alignment (TA) indicator across the P-wave search window. For example, the one or more processors correlate a P-wave template to a subsegment of the segment of CA signals within the P-wave search window to obtain a subsegment correlation value. In accordance with the operations at 308-316, the correlation is iteratively performed for subsegments of the CA signals along the P-wave search window to obtain a TA indicator (e.g., correlation function) defined by a collection of corresponding subsegment correlation values. The collection of subsegment TA indicator values define a function across the P-wave search window indicating a degree of temporal correlation between the P-wave template and a corresponding subsegment of the CA signals. The correlation function represents a temporal alignment indicator indicative of a level or degree of temporal alignment between the template and the CA signals. FIGS. 5 and 6 show examples of CA signals temporal alignment (correlation functions) and amplitude dependence indicators (covariance functions) with respect to a select P-wave template.

By way of example, the one or more processors may apply a Pearson's r correlation algorithm or other correlation measurements such as Kendell or Spearman correlations. The one or more processors align the template over a time range and perform the calculation shown in Equation 1:

$$r^2 = \frac{\sum x_i y_i}{\sqrt{\sum x_i^2 \sum y_i^2}}.$$ Equation 1

The variable $x_i$ corresponds to the data samples within the CA signals, while the variable $y_i$ corresponds to values along the template. Each value of Pearson's r, is calculated by applying Equation 1 over a number of data samples corresponding to the width of the P-wave template. For example, when the P-wave template includes 50 data points, each value of r is collected by applying Equation 1 over i=1 to i=50, for the current subsegment of 50 data samples from the CA signals aligned with the P-wave template. Each time the template is shifted along the CA signals, a new value for r is calculated, again by stepping through the range of i=1 to i=50 to apply the P-wave template to the current subsegment of CA signals. The operations at 308 are repeated to apply equation 1 at every point in time for each sample of the CA signal in the current subsegment over the width of the template. When the template overlaps with the P-wave, the correlation approaches 1. When the template overlaps noise, the correlation approaches a value significantly lower than 1 (e.g., 0.8) to even −1. The width of the template may be varied but is typically about 50 data samples when the sampling rate is 500 Hz or 512 Hz.

Optionally, the temporal alignment indicator may be determined in other manners when applying the P-wave template to the CA signals. By way of example, the TA indicator may be determined based on a root mean square (RMS) function which represents an error-based template matching relation between the P-wave template and subsegments of the CA signals. Temporal alignment is achieved when the RMS error is minimized. Different functions for calculating a TA indicator may be utilized depending upon the nature of the underlying CA signals, such as whether the CA signals exhibit baseline drift or not. An alternative to the RMS error is to sum absolute value of the difference of each point in the candidate P-wave and the template. Choice of TA indicator is primarily influenced by computational efficiency.

Optionally, the applying operation at 308 may be performed in connection with an ensemble average (as explained below in connection with FIG. 3B). For example, the applying the P-wave template to the sub-segments of the CA signals may further comprise: i) identifying an R-wave COI from one or more beats in the series of beats; ii) applying the P-wave search window to the sub-segments of the CA signals prior the R-wave COI for the one or more beats; iii) performing an ensemble average of the CA signals within the P-wave search window for the one or more beats; and iv) calculating a correlation of the ensemble average with the P-wave template to obtain the TA indicator.

At 312, the one or more processors analyze the temporal alignment indicator based on a first criteria. For example, the first criteria may be a largest peak in the correlation function across the CA signals in the search window. For example, the one or more processors determine whether a peak of the correlation function at the present point in time exceeds a correlation threshold and exceeds a prior "best" (e.g., largest) subsegment correlation peak. If the peak of the current correlation function does not exceed a correlation threshold and/or does not a prior best subsegment correlation peak, flow moves to 314. If the peak of the current correlation function exceeds a correlation threshold and exceeds a prior best subsegment correlation peak, flow moves to 313, where the current peak is saved as the new best/largest peak of the correlation function. At 313, the locate within the CA signals, corresponding to the new peak, is also saved as a new peak location. At 313, the one or more processors track a desired (e.g., best, closest or largest) temporal alignment indicator within the P-wave search window. Flow continues to 314.

At 312, a threshold is used to avoid saving too low/small of a peak value. Optionally, the threshold may be omitted entirely, and the decision at 312 based solely on the comparison to a prior best peak.

As a nonlimiting example, the correlation threshold may be 0.75. The threshold may be preprogrammed and/or may be automatically updated based on subsegment correlation values calculated over time. For example, over time, it may be determined, manually or automatically, that a correlation threshold of 0.75 results in under-detection or over-sensing of P-waves. Based thereon, the correlation threshold may be decreased or increased, manually or automatically. Additionally or alternatively, the correlation threshold may be defined as a function of a moving average of correlation peaks for actual P-waves that are identified in accordance with embodiments herein. For example, over time, an average for correlation peaks for X actual P-waves may be determined and the correlation threshold set to be a percentage of the average (e.g., 80%) or by subtracting a predetermined amount from the average (e.g., average −0.25).

At 314, the one or more processors determine whether the analysis should be repeated for the next subsegment of the CA signals within the search window.

When the processor determines to repeat the analysis for the next subsegment, flow continues to 316. At 316, the one or more processors shift the P-wave template along the CA signals to the next subsegment start time. For example, the P-wave template may be shifted forward one sample, five samples or in other predetermined number of samples. Additionally or alternatively, the P-wave template may be shifted forward by a predetermined amount of time. Additionally or alternatively, the P-wave template may be shifted forward based on content of the prior subsegment. For example, a prior subsegment may exhibit a certain amount of correlation at a point in time and/or data sample. Based on the amount of correlation in the prior subsegment, the P-wave template may be shifted forward to have some level of alignment with respect to the correlation at the point of in time of interest in the prior subsegment.

From 316, flow returns to 308 where the P-wave template is correlated to the CA signals within the new subsegment. The operations at 308-316 are repeated, until the decision is made at 314 to stop repeating. For example, the end of the search window may have been reached, in which case no further sub segments exist to be analyzed.

Alternatively, other reasons may be utilized to decide when to stop analyzing sub segments of the CA signals. By way of example, the one or more processors may determine that a P-wave is not present. In accordance with at least some embodiments, when a P-wave is absent from an expected location, in combination with an undue level of RR variability, the process may declare an atrial fibrillation (AF) episode. When excessive RR interval variability is present and P-waves are absent, among other things, the one or more processors may increase the specificity of the process. For example, the specificity may be increased by changing one or more sensing thresholds, as well as adjusting one or both of the first and second criteria.

Returning to 314, when the one or more processors determined that no more subsegments should be analyzed, flow skips to 318. The operations at 308-316 identify the first criteria as a maximum for the TA indicator over the P-wave search window, wherein the candidate P-wave corresponds to the subsegment of the CA signal for which the corresponding TA indicator has the maximum At 318, the one or more processors designate a candidate P-wave based on temporal alignment indicator saved at 313. The candidate P-wave represents the subsegment within the P-wave search window that satisfied the criteria 1 at 312 and was last saved at 313. The candidate P-wave may represent a P-wave peak or morphology that exhibits a desired degree of correlation to the P-wave template as designated by the temporal alignment indicator.

At 320, the one or more processors calculating an amplitude dependence (AD) indicator based on the temporal alignment indicator. The AD indicator is indicative of a level or degree of amplitude match between the candidate P-wave AD indicator and the P-wave template AD indicator. For example, the AD indicator may represent a covariance function based on the numerator of the correlation function. The AD indicator (e.g., covariance function) is used as a second criteria that is calculated by the one or more processors. The second criteria measures the amplitude of the CA signals in relation to the P-wave template. For example, the covariance function may represent a covariance amplitude for a corresponding subsegment of the CA signals. With reference to equation 1, the numerator, $\Sigma x_i y_i$, represents the covariance between the template and the corresponding subsegment of the CA signals. If the covariance is divided by root mean square value of the template, $\sqrt{\Sigma y_i^2}$, the results is equation 2:

$$covamp = \frac{\sum x_i y_i}{\sqrt{\sum y_i^2}}. \qquad \text{Equation 2)}$$

The covamp measures the amplitude of the CA signals and the corresponding subsegment in relation to the template. At 320, the one or more processors calculate covamp at each data point (corresponding to a particular point in time) along the current corresponding subsegment of CA signals. For any given template $\sqrt{\Sigma y_i^2}$, is a constant. Consequently, normalizing the covariance by the root mean square value of the template in not necessary but is convenient for comparison purposes.

At 322, the one or more processors compare the AD indicator with a second criteria. For example, the one or more processors determine whether the covariance function for the candidate P-wave is within a tolerance range of a covariance threshold (e.g., a covariance amplitude peak, also referred to as covampmax) for a reference P-wave (criteria 2). The reference P-wave may represent the P-wave template used in the correlation analysis. The covampmax represents a magnitude of the covariance amplitude (covamp) at the P-wave correlation peak. The covampmax may be calculated once when template is extracted or may be updated by a moving average. By way of example, the tolerance range may be 1.5×covampmax to about 0.5×covampmax. Additionally or alternatively, the covariance threshold (covampmax) may be automatically adapted to different values with respect to different postures.

When the AD indicator (e.g., covariance function) is not within the tolerance range, the one or more processors determine that both criteria have not been satisfied for the current beat or ensemble of beats and the candidate P-wave is declared invalid or a false P-wave and the process ends for the current beat or ensemble of beats. When the AD indicator (e.g., covariance function) is below a lower limit of the tolerance range, this is an indicator that there is a very low or no scaler relation of the amplitude of the P-wave template and the current sub-segment. When the AD indicator (e.g., covariance function) is above an upper limit of the tolerance range, this is an indicator that the scaler relation has exceeded an upper limit for total or optimal amplitude correlation between the P-wave template and the current subsegment, and thus some other error is present in the LA indicator, thereby justifying throwing out or disregarding the current candidate P-wave. When the AD (e.g., covariance function) is within the tolerance range, the one or more processors determine that both criteria have been satisfied for the current beat or ensemble of beats flow, moves to 324.

Optionally, the amplitude dependence indicator may be determined in manners other than based on a covariance function, provided the function affords an indication of a relation between the amplitude of the P-wave template and the amplitude of the candidate P-wave (identified at 318). Another amplitude criteria that may be used include using the root mean squared error between the template and the candidate P-wave (RMS error). When the RMS error is below a threshold then the algorithm deems the candidate P-wave as an actual P-wave. An alternative to the RMS error is to sum absolute value of the difference of each point in the candidate P-wave and the template. Another alternative metric of amplitude is the RMS magnitude of the candidate P-wave. If the difference between the RMS of the Template and the RMS of the candidate P-wave, the P-wave is deemed as an actual P-wave.

At 324, the one or more processors designate the candidate P-wave as an actual P-wave and record the designation of the actual P-wave. In accordance with the foregoing operations, embodiments herein identify a true P-wave when both of the TA indicator and the AD indicator satisfy a corresponding threshold and range, respectively.

The foregoing operations at 308-322 are described in connection with a somewhat serial manner in which the TA indicator is obtained and analyzed with respect to the first criteria first, followed by the calculation of the AD indicator and comparison of the AD indicator to the second criteria. Additionally or alternatively, the operation at 308-322 may be implemented in parallel manner in which the TA indicator and AD indicator are determined in parallel. The TA indicator and AD indicator are also compared in parallel to corresponding first and second criteria.

In some instances, the method of FIG. 3A may experience challenges when run in real time to find an optimal TA indicator. However, very good alignment can be achieved using only the R-wave COI as a reference for setting the preceding P-wave window from CA. The variation in the P-R interval is only about 5 to 10%. Consequently, an alternative approach may be implemented.

Figure 3B:
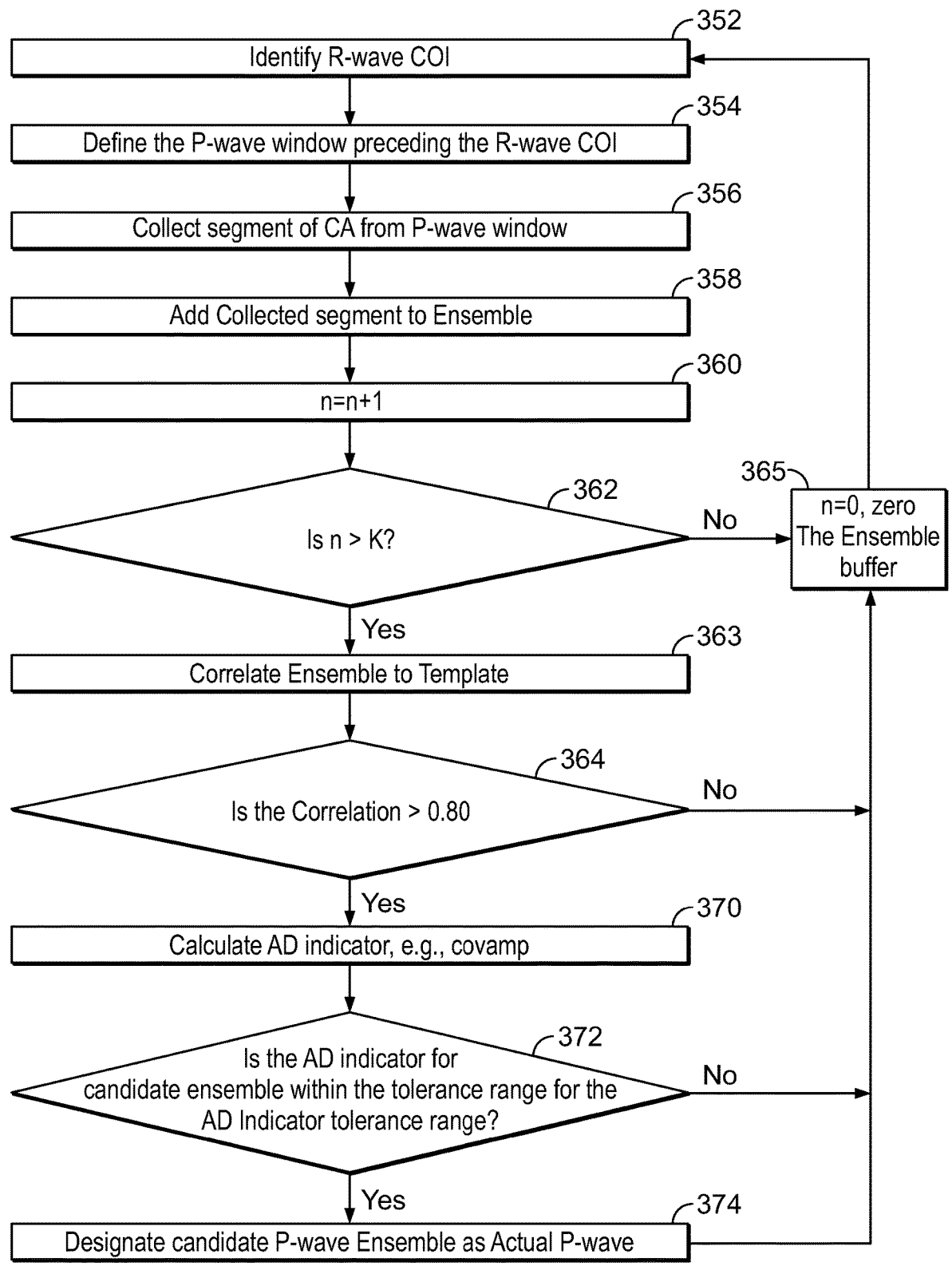
FIG. 3B illustrates an alternative approach in accordance with embodiments herein.

FIG. 3B illustrates an alternative approach in accordance with embodiments herein. The operations of FIG. 3B are performed by one or more processors. At 352, the one or more processors identify the R-wave COI from a beat in a series of beats. At 354, the one or more processors define the P-wave window to overlay the subsegment of the CA signals at a predetermined time prior to the R-wave COI for the corresponding beat. For example, the P-wave window may be set to overlay a subsegment of the CA signals that is Xms prior to the peak of the R-wave. At 356, the one or more processors collect the subsegment of the CA signals overlaid by the P-wave search window at 358, the one or more processors add the subsegment collected at 356 to an ensemble of subsegments. At 360, the n, the ensemble average segment counter is incremented. At 362, the number of P-wave segments added the ensemble is tested to see if it exceeds the number of desired segments, K, added to the ensemble. K may vary from 1 or a relatively small number, such as when the P-waves are relatively large and the signal to noise is relatively high. Alternatively, K may be set to a relatively large number, when P-waves are very small or if noise is excessive. For example, the P-wave ensemble may include 256 elements (K=256) resulting in dramatically enhancing the S/N ratio by 16×. Flow moves from 360 to back to 352, such that the identifying, defining and collecting operations are repeated a predetermined number of times (until n>K) to form an ensemble average of the CA signals within the P-wave search window for a series of beats.

Alternatively, at 362, when n>K, then the ensemble average has been completed. At 363, the one or more processors perform a correlation operation in which the ensemble average is correlated with the P-wave template. The completed ensemble is correlated to the P-wave template at 363. The correlation represents an alignment indicator indicative of whether the ensemble of segments have a shape that is aligned with a shape of the P-wave template. At 364, the one or more processors analyze the alignment indicator based on a first criteria. For example, the one or more processors test the alignment indicator (correlation) to determine if the alignment indicator meets or exceeds a threshold (the first criteria). By way of example, the threshold may be set to 0.8. When the alignment indicator (correlation) does not exceed the threshold, flow moves to 365. At 365, the ensemble buffer is set to zero (n=0) in the operations at 352-364 repeated for the next series of beats.

Alternatively, when the alignment indicator satisfies the first criteria, namely when the correlation exceeds the threshold, flow moves to 370 at 370, the one or more processors calculate an amplitude dependence (A/D) indicator (covamp) by simply multiplying the correlation by $\sqrt{\Sigma x_i^2}$. This result is represented in Equation 2. At 372, the one or more processors compare the AD indicator to a second criteria. For example, the covamp is tested to determine if it is within the tolerance range for an AD indicator. If the AD indicator does not satisfy the second criteria, the current candidate P-wave is determined to not be an actual P-wave, and flow moves from 372 back to 365 where the ensemble buffer is reset to zero.

Alternatively, at 372, if the covamp is within range, flow moves to 374. At 374, the one or more processors determined that the P-wave ensemble is accepted as an actual P-wave. Thereafter, at 365, n is set to zero and the ensemble average is zeroed out. The process of FIG. 3B illustrates an alternative approach that is well suited to be implemented in real time.

Figure 4:
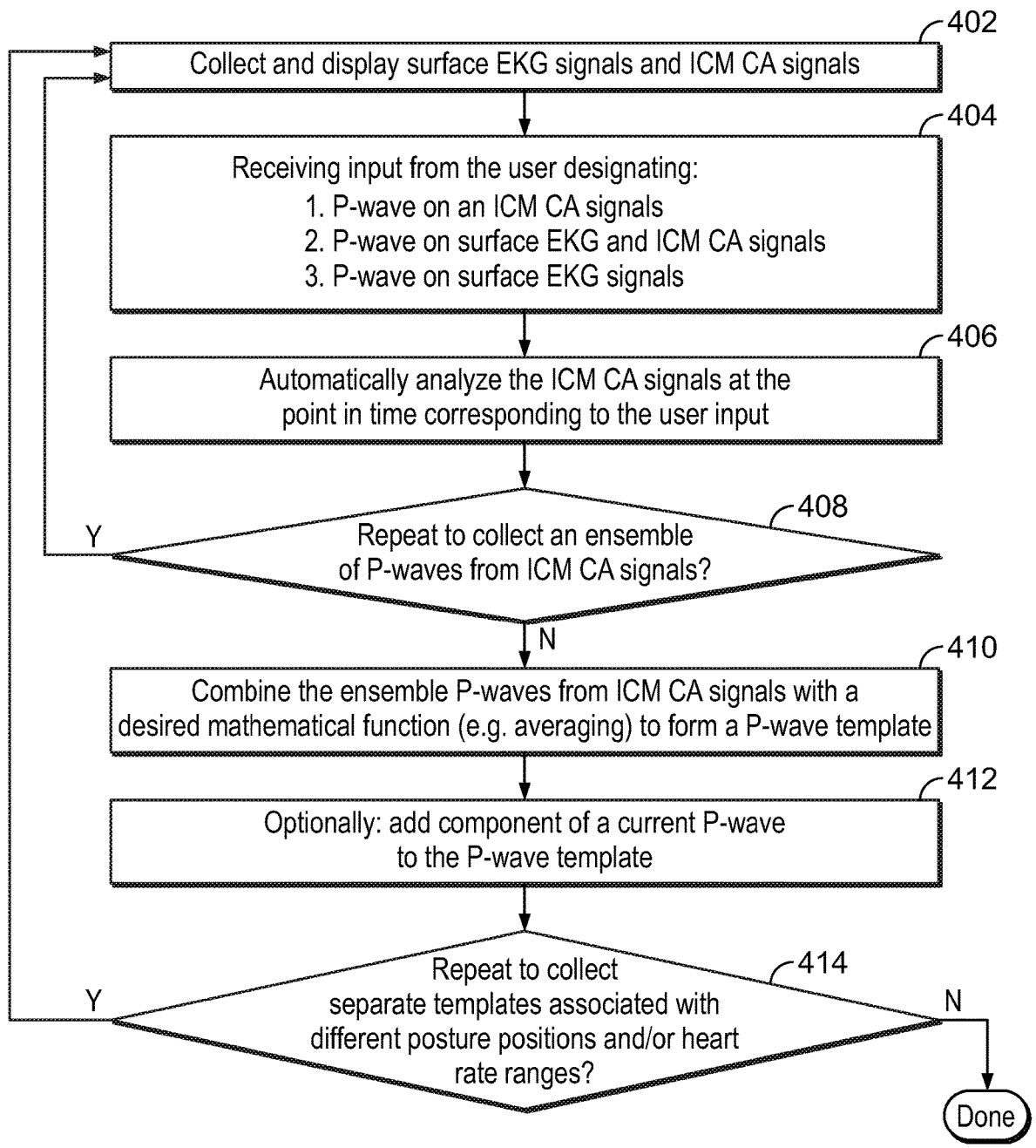
FIG. 4 illustrates a process for acquiring one or more P-wave templates in accordance with embodiments herein.

FIG. 4 illustrates a process for acquiring one or more P-wave templates in accordance with embodiments herein. The process of FIG. 4 may be implemented by one or more processors of an ICM, an external device, a physician's programmer and/or at a remote server. For example, the P-wave templates may be generated by a physician's programmer during a patient physician visit, and/or based on historical information about the current patient and/or a patient population. As another example, the P-wave template may be generated by the ICM in response to an instruction received from an external device, periodically (e.g., once a month while the patient is asleep) and/or based on arrhythmia determinations made by the ICM. For example, the ICM may automatically initiate a process to obtain new P-wave templates when an ICM does not identify any new arrhythmias for an extended period of time and/or continuously identifies arrhythmias for an extended period of time, either of which may be related to under-sensing or over-detecting P-waves. The process of FIG. 4 may be applied real time during the initial in clinic setup and/or continuously on a day-by-day basis. The process of FIG. 4 may create different averaged templates for individual designated postures and/or heart rate ranges. FIG. 4 may be implemented with other types of IMDs, not just ICMs.

At 402, the one or more processors collect and display surface electrocardiogram (EKG) signals and CA signals collected by an implantable medical device, such as an intracardiac electrogram (IEGM). For example, a set of surface electrodes may be attached to a patient from which the surface EKG signals are collected, while the ICM simultaneously collects CA signals (IEGM) from implanted electrodes. The surface EKG signals and ICM CA signals are co-displayed (e.g., on a programmer or other external device). It is recognized that the collection of the surface EKG signals and ICM CA signals may occur at an earlier point in time, with both sets of signals subsequently displayed to a physician. For example, the EKG and CA signals may be collected at one point in time (e.g., at home while a patient follows a predetermined series of instructions or during a clinical visit with the assistance of medical personnel). At the same time or at a later time, the same or different physician (at the same location or at a different remote location) may then analyze the EKG and CA signals.

At 404, in connection with the physician's analysis of the EKG and CA signals, the physician enters an input designating information indicative of P-waves. For example, the one or more processors of a programmer or other external device may receive an input from a user that designates at least one of: 1) P-waves in intracardiac electrogram (IEGM) signals collected by an implantable medical device (IMD), 2) P-waves in surface EKG signals and on the IEGM signals, and 3) P-waves on surface EKG signals. For example, a clinician may use a graphical user interface to select points corresponding to P-waves along in EKG strip and/or the IEGM. In connection there with, the one or more processors identify the segment of the IEGM that includes the corresponding P-waves. For example, the one or more processors may center a P-wave window over the point in time at which the physician has designated each P-wave. The window may have a predetermined width or may be adjustable in width by the user.

At 406, the one or more processors automatically analyze the IEGM signals (CA signals) within the window for the time period corresponding to the user input. For example, when the user designates the P-waves directly on the ICM CA signals, the analysis may simply record the data points along the P-wave window from the ICM CA signals. Additionally or alternatively, when user designates the P-waves directly on the ICM CA signals as well as on the surface EKG signals, the analysis may include the additional operation of aligning the P-wave window based on both sources of user inputs. Additionally or alternatively, when the user designates to P-waves only on the surface EKG signals, the analysis may include identifying a corresponding P-wave window to align over the ICM CA signals. The P-wave window is aligned on the ICM CA signals contemporaneous in time with the P-wave designated on the surface EKG signals. It is recognized that additional operations may be performed in the analysis, such as filtering of the signals, removal of noise and the like.

At 408, the one or more processors determine whether to repeat the operations at 402-406 in connection with additional cardiac beats. If so, flow returns to 402 and the operations at 402-406 are repeated to collect an ensemble of P-waves from ICM CA signals. Once the desired number of cardiac beats are analyzed, flow moves from 408 to 410.

At 410, the one or more processors combined the collection of P-waves from the CA signals utilizing a desired mathematical function to form a P-wave ensemble. For example, the collection of P-waves may be combined through averaging, weighted averaging and the like.

At 412, an optional operation may be added. At 412, the one or more processors may modify the P-wave template by adding a current P-wave and/or one or more recent P-waves. For example, when ensemble averaging is utilized to form a P-wave template, the ensemble average may include one or more recent P-waves that have been identified.

At 414, the one or more processors determine whether to repeat the operations of 402-412 in connection with additional patient posture positions and/or different heart rates. For example, the operations at 402-412 may be implemented while a patient is standing, while a patient is sitting, while a patient is lying on his/her back, while a patient is lying on each side, and the like. As another example, the operations of 402-412 may be implemented to collect different templates for different heart rate ranges. By repeating the process of FIG. 4 in connection with different posture positions and/or heart rate ranges, embodiments herein allow for different templates to be developed in connection with different postures and different heart rate ranges.

Additionally or alternatively, the operations of FIG. 4 may be implemented separately in order to account for migration and other movement of an ICM within an implantation pocket. For example, when ICM is implanted in a pectoral area, over time, the ICM may rotate along various axes and thus become oriented differently within a patient, relative to different postures. For example, at the time of implant, an ICM may be substantially oriented vertically while a patient is standing up and substantially oriented horizontally while a patient is lying down. However, overtime the ICM may migrate within the pocket such that, when a patient is standing up or lying down, the ICM is no longer in the original corresponding vertical or horizontal orientation. Accordingly, the operations of FIG. 4 may be repeated when the potential exists that an ICM has migrated, to acquire one or more new templates.

Optionally, embodiments herein may be implemented with devices other than ICMs, such as a subcutaneous ICD, a transvenous ICD, a leadless device, and the like. The template acquisition process of FIG. 4 may be repeated in connection with each of the foregoing types of implantable medical devices at different points in time throughout the life of the medical device. For example, a subcutaneous patch may shift, experience scar tissue growth or otherwise experience changes that warrant collection of new templates. Similarly, a transvenous ICD or a leadless device may also experience changes over time (e.g., growth of scar tissue at electrodes, shifts and electrode position) that warrant acquisition of new templates. Finally, regardless of the implantable device, it may be desirable to acquire new templates, simply when a patient's physiologic behavior changes over time.

FIG. 5 illustrates a first example of a CA signal, a TA indicator (e.g., correlation function) and AD indicator (e.g., covariance function) determined in accordance with embodiments herein. The CA signal 500 is collected by an ICM. The CA signal 500 includes R-waves 501, a T-wave 505 and a P-wave 503. The T-wave 505 has a wide wave shape, while the P-wave 503 is extremely diminutive or arguably indiscernible. The bottom tracing 511 is the correlation of the CA signal 500 and a P-wave template. At the point labelled as 509, the correlation value is approximately 0.95. The middle tracing 507 represents a cross-correlation between the P-wave template and the CA signal divided by the root mean square value of the P-wave template. The point 508 is the location at which the covamp is measured.

FIG. 6 illustrates a second example of a CA signal, correlation function and covariance function determined in accordance with embodiments herein. The CA signal 600 is collected by an ICM. The CA signal 600 includes R-waves 601. The bottom tracing 611 is the correlation of the CA signal 600 and a P-wave template. The middle tracing 607 represents a cross-correlation between the P-wave template and the CA signal divided by the root mean square value of the P-wave template. The vertical lines 602 and 604 represent the points at which a P-wave is identified. Again note that the P-wave is very small and cannot easily be identified on the top CA signal trace, but the algorithms described herein still locate the P-waves. At 602 and 604, the correlation function has values of 0.91 and 0.75, respectively, while the cross-correlation function exhibits a slight increase.

Figure 7A:
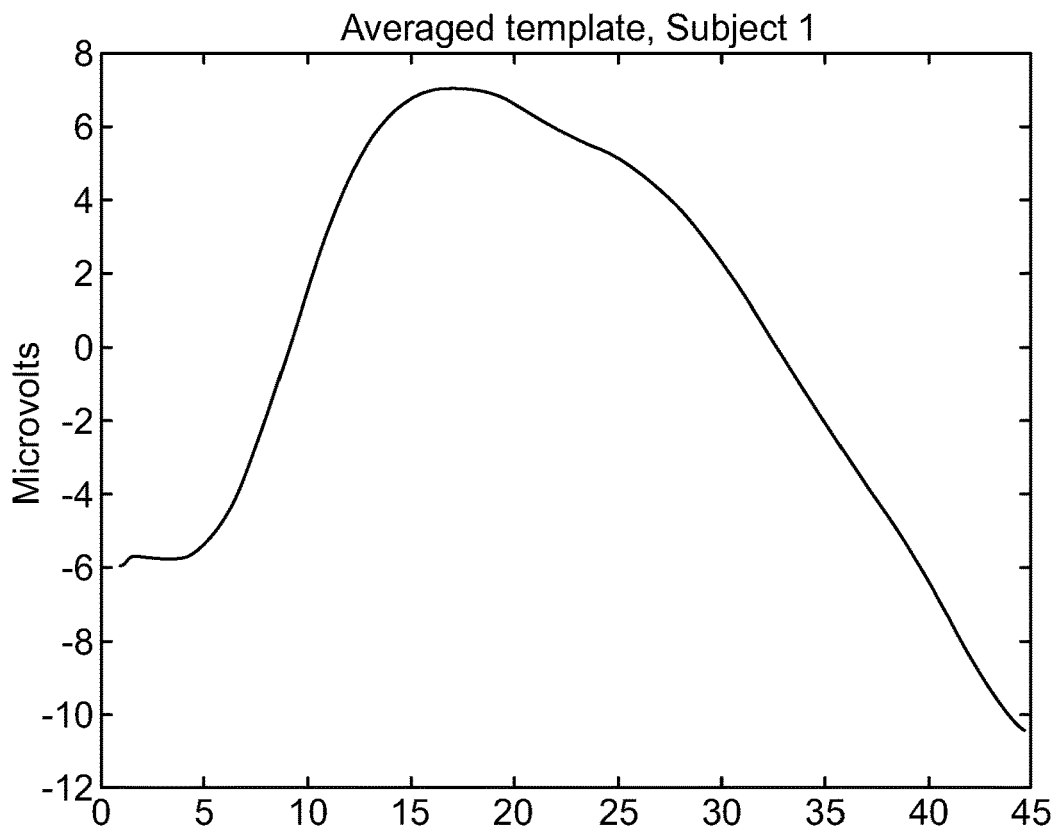
FIG. 7A illustrates example P-wave templates that may be derived for different patients in accordance with embodiments herein.
Figure 7B:
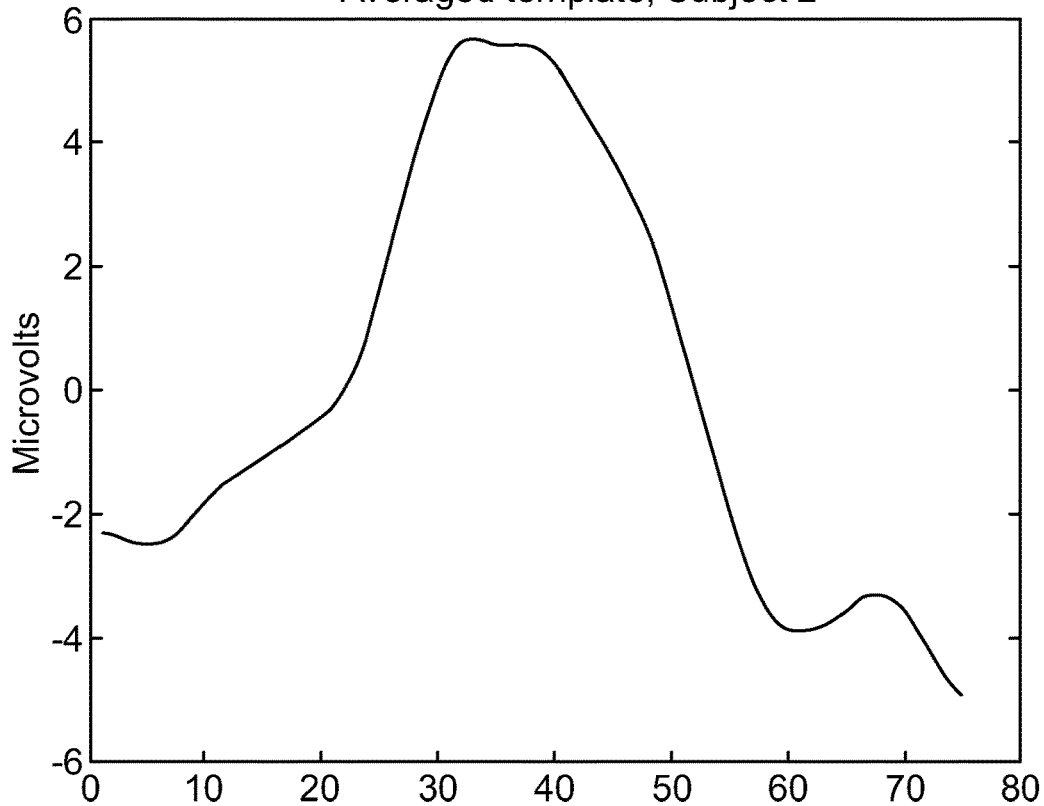
FIG. 7B illustrates example P-wave templates that may be derived for different patients in accordance with embodiments herein.
Figure 7C:
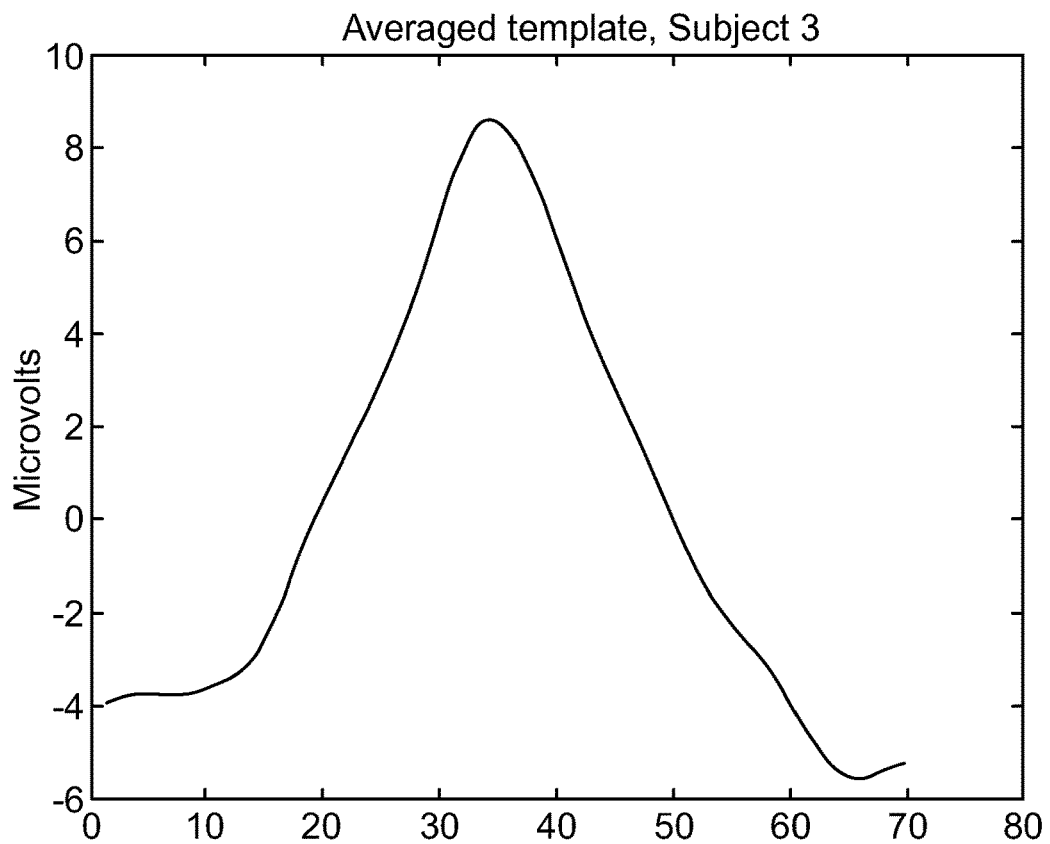
FIG. 7C illustrates example P-wave templates that may be derived for different patients in accordance with embodiments herein.

FIGS. 7A-7C illustrate example P-wave templates that may be derived for different patients in accordance with embodiments herein. Note the signatures are quite different. An algorithm can simply include selected P-waves into a moving average to create an average template. An average template is superior to using a single operator selected template. This process may be applied real time during the initial in clinic setup and/or continuously on a day-by-day basis. An algorithm may create different averaged templates for each designated posture.

Figure 9:
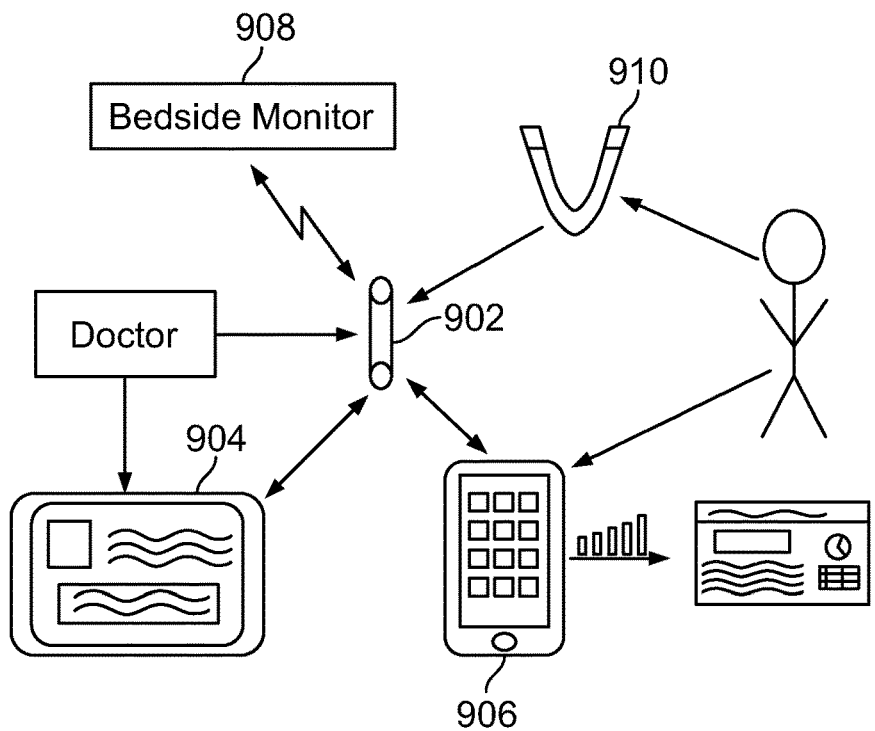
FIG. 9 illustrates a system level diagram indicating devices and networks in accordance with embodiments herein.

FIG. 9 illustrates a system level diagram indicating devices and networks that may utilize the methods and systems herein. For example, an implantable cardiac monitoring device (ICM) 902 may be utilized to collect a cardiac activity data set, including identification of false versus actual the P waves in accordance with embodiments herein. The ICM 902 adds P-wave markers to the CA data set in connection with valid/actual P waves. Optionally, the ICM 902 may collect information regarding false P waves there were identified by alternative detection and confirmation algorithms implemented within the ICM. The ICM 902 may supply the CA data set (CA signals and DD feature markers) to various local external devices, such as a tablet device 904, a smart phone 906, a bedside monitoring device 908, a smart watch and the like. The devices 904-908 include a display to present the various types of CA signals, markers, statistics, diagnostics and other information described herein. The ICM 902 may convey the CA data set over various types of wireless communications links to the devices 904, 906 and 908. The ICM 902 may utilize various communications protocols and be activated in various manners, such as through a Bluetooth, Bluetooth low energy, Wi-Fi or other wireless protocol. Additionally or alternatively, when a magnetic device 910 is held next to the patient, the magnetic field from the device 910 may activate the ICM 902 to transmit the cardiac activity data set and AF data to one or more of the devices 904-908.

The processes described herein for analyzing the cardiac activity signals to identify P waves, may be implemented on one or more of the devices 904-908. Additionally or alternatively, the ICM 902 may also implement the processes described herein. The devices 904-908 may present the CA data set and AF detection statistics and diagnostics to clinicians in various manners. As one example, AF markers may be illustrated on EGM signal traces. AF, P-wave, R-wave and other sinus markers may be presented in a marker channel that is temporally aligned with original or modified CA signals. Additionally or alternatively, the duration and heart rate under AF may be formatted into histograms or other types of charts to be presented alone or in combination with CA signals.

Figure 10:
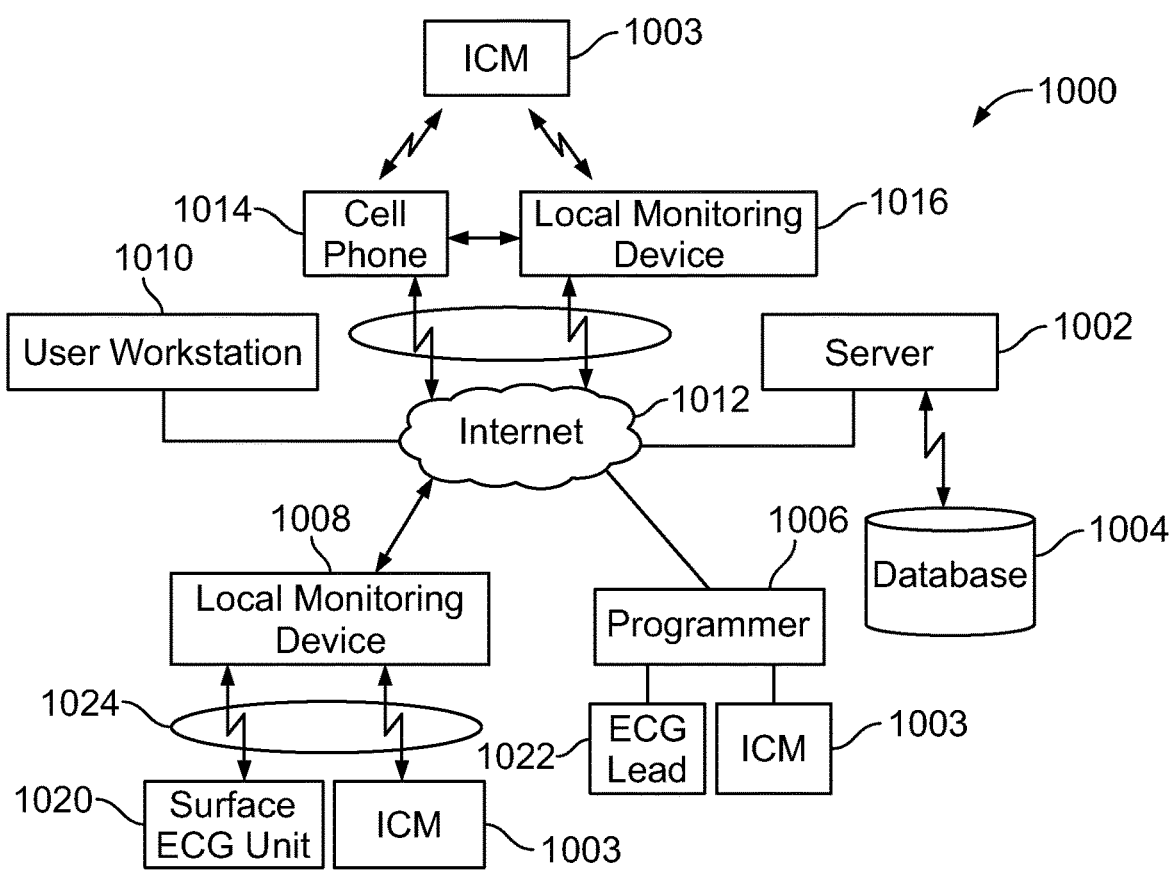
FIG. 10 illustrates a distributed processing system in accordance with embodiments herein.

FIG. 10 illustrates a distributed processing system 1000 in accordance with embodiments herein. The distributed processing system 1000 includes a server 1002 connected to a database 1004, a programmer 1006, a local monitoring device 1008 and a user workstation 1010 electrically connected to a network 1012. Any of the processor-based components in FIG. 10 (e.g., workstation 1010, cell phone 1014, local monitoring device 1016, server 1002, programmer 1006) may perform the processes discussed herein.

The network 1012 may provide cloud-based services over the internet, a voice over IP (VoIP) gateway, a local plain old telephone service (POTS), a public switched telephone network (PSTN), a cellular phone based network, and the like. Alternatively, the communication system may be a local area network (LAN), a medical campus area network (CAN), a metropolitan area network (MAN), or a wide area network (WAM). The communication system serves to provide a network that facilitates the transfer/receipt of data and other information between local and remote devices (relative to a patient). The server 1002 is a computer system that provides services to the other computing devices on the network 1012. The server 1002 controls the communication of information such as cardiac activity data sets, bradycardia episode information, asystole episode information, AF episode information, markers, cardiac signal waveforms, heart rates, and device settings. The server 1002 interfaces with the network 1012 to transfer information between the programmer 1006, local monitoring devices 1008, 1016, user workstation 1010, cell phone 1014 and database 1004. The database 1004 stores information such as cardiac activity data, AF episode information, AF statistics, diagnostics, markers, cardiac signal waveforms, heart rates, device settings, and the like, for a patient population. The information is downloaded into the database 1004 via the server 1002 or, alternatively, the information is uploaded to the server 1002 from the database 1004. The programmer 1006 may reside in a patient's home, a hospital, or a physician's office. The programmer 1006 may wirelessly communicate with the ICM 1003 and utilize protocols, such as Bluetooth, GSM, infrared wireless LANs, HIPERLAN, 3G, satellite, as well as circuit and packet data protocols, and the like. Alternatively, a telemetry "wand" connection may be used to connect the programmer 1006 to the ICM 1003. The programmer 1006 is able to acquire ECG 1022 from surface electrodes on a person (e.g., ECGs), electrograms (e.g., EGM) signals from the ICM 1003, and/or cardiac activity data, AF episode information, AF statistics, diagnostics, markers, cardiac signal waveforms, atrial heart rates, device settings from the ICM 1003. The programmer 1006 interfaces with the network 1012, either via the internet, to upload the information acquired from the surface ECG unit 1020, or the ICM 1003 to the server 1002.

The local monitoring device 1008 interfaces with the communication system to upload to the server 1002 one or more of cardiac activity data set, AF episode information, AF statistics, diagnostics, markers, cardiac signal waveforms, heart rates, sensitivity profile parameter settings and detection thresholds. In one embodiment, the surface ECG unit 1020 and the ICM 1003 have a bi-directional connection 1024 with the local RF monitoring device 1008 via a wireless connection. The local monitoring device 1008 is able to acquire cardiac signals from the surface of a person, cardiac activity data sets and other information from the ICM 1003, and/or cardiac signal waveforms, heart rates, and device settings from the ICM 1003. On the other hand, the local monitoring device 1008 may download the data and information discussed herein from the database 1004 to the surface ECG unit 1020 or the ICM 1003.

The user workstation 1010 may be utilized by a physician or medical personnel to interface with the network 1012 to download cardiac activity data and other information discussed herein from the database 1004, from the local monitoring devices 1008, 1016, from the ICM 1003 or otherwise. Once downloaded, the user workstation 1010 may process the CA data in accordance with one or more of the operations described above. The user workstation 1010 may upload/push settings (e.g., sensitivity profile parameter settings), ICM instructions, other information and notifications to the cell phone 1014, local monitoring devices 1008, 1016, programmer 1006, server 1002 and/or ICM 1003. For example, the user workstation 1010 may provide instructions to the ICM 1003 in order to update sensitivity profile parameter settings when the ICM 1003 declares too many false AF detections.

The processes described herein in connection with analyzing cardiac activity data for detecting R-waves/noise and for confirming or rejecting AF detection may be performed by one or more of the devices illustrated in FIG. 10, including but not limited to the ICM 1003, programmer 1006, local monitoring devices 1008, 1016, user workstation 1010, cell phone 1014, and server 1002. The process described herein may be distributed between the devices of FIG. 10.

The systems of FIGS. 9 and 10 may be implemented in connection with calculating P-wave templates as described herein. For example, the CA signals represent intracardiac electrograms (IEGM), one or more of the devices, phones, workstations, servers and the like in FIGS. 9-10 may include a display configured to display on a graphical user interface (GUI) IEGM signals and surface electrocardiogram (EKG) signals. One or more of the devices, phones, workstations and the like may receive a user input from the GUI an input designating at least one of: 1) P-waves on the IEGM signals, 2) P-waves on surface EKG signals and P waves on the IEGM signals, or 3) P-waves on the surface EKG signals. The user input designates select points corresponding to the P-waves. The one or more of the devices, phones, workstations, servers and the like identify the segment of the CA signals that includes the corresponding P-waves.

The systems and devices of FIGS. 9 and 10 may repeat the displaying, receiving and identifying to calculate a plurality of P-wave templates associated with different postures and utilizing a select one of the P-wave templates based on a current posture of the patient when the CA signals are collected. The systems and devices of FIGS. 9 and 10 may calculate separate P-wave templates corresponding to a patient standing, the patient sitting, the patient lying on his/her back, and the patient lying on each side.

Application of Current P-Wave Detection Embodiments within Other Monitoring, Detection and Therapy Processes The P wave detected processes described in accordance with embodiments herein may be integrated into and utilized with various monitoring processes, arrhythmia detection processes, therapy delivery processes and the like.

Figure 11A:
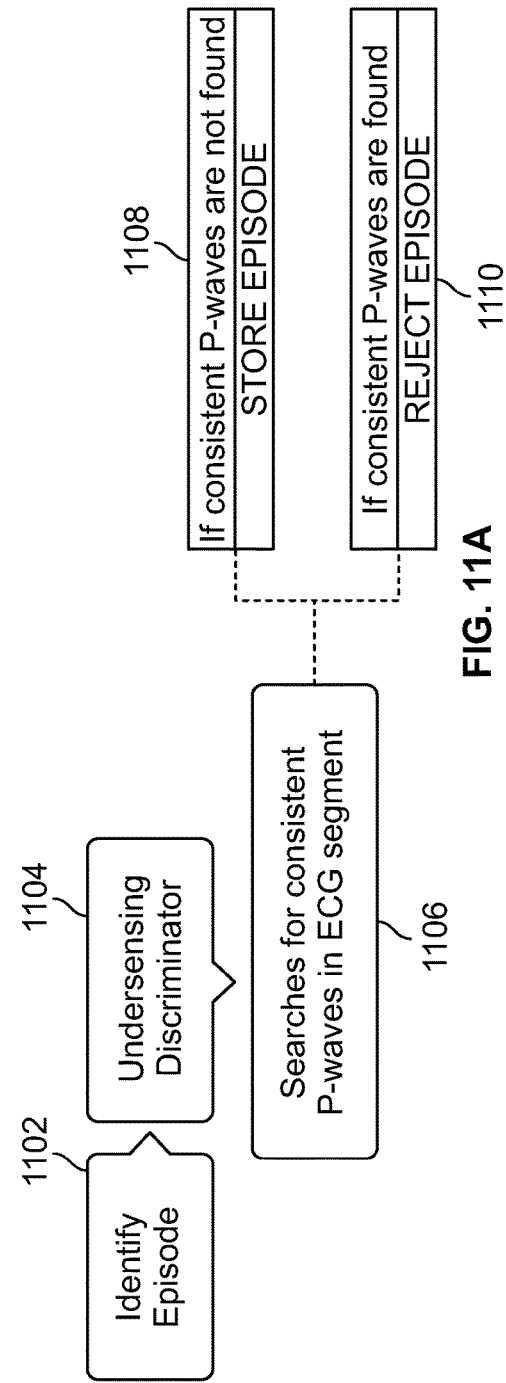
FIG. 11A illustrates a process in which the P-wave detection processes described herein may be implemented in connection with detecting atrial fibrillation.

FIG. 11A illustrates a process in which the P-wave detection processes described herein may be implemented in connection with detecting arrhythmia episodes, including, but not limited to, syncope, bradycardia and atrial fibrillation (AF) episodes. At 1102, an arrhythmia detection algorithm monitor CA signals to identify arrhythmia episodes. As nonlimiting examples, one or more processors of an implantable medical device may collect CA signals, identify in R-wave Cal in connection with each beat (e.g., a peak of an R-wave) and measure RR intervals between successive R wave COIs. The one or more processors may then analyze variations in the RR intervals between successive R waves. Based at least in part on variability of the RR intervals, the one or more processors may declare an arrhythmia episode (e.g., syncope, bradycardia and AF episodes). By way of example, the arrhythmia detection operation 1102 may be implemented in accordance with one or more of the methods and systems described in the following co-pending applications (all of which are expressly incorporated herein by reference in their entireties): U.S. patent application Ser. No. 15/973,126, titled "METHOD AND SYSTEM FOR SECOND PASS CONFIRMATION OF DETECTED CARDIAC ARRHYTHMIC PATTERNS"; U.S. patent application Ser. No. 15/973,351, titled "METHOD AND SYSTEM TO DETECT R-WAVES IN CARDIAC ARRHYTHMIC PATTERNS"; U.S. patent application Ser. No. 15/973,307, titled "METHOD AND SYSTEM TO DETECT POST VENTRICULAR CONTRACTIONS IN CARDIAC ARRHYTHMIC PATTERNS"; and U.S. patent application Ser. No. 16/399,813, titled "METHOD AND SYSTEM TO DETECT NOISE IN CARDIAC ARRHYTHMIC PATTERNS". When a candidate arrhythmia episode is identified, a portion of the CA signals are stored at least temporarily in memory of the IMD. For example, when an arrhythmia episode is detected, a segment of EGM signals may be stored for a predetermined period of time (e.g., 30 seconds, 1 minute, 5 minutes, etc.). Additionally or alternatively, the duration of the segment of EGM signals that is stored may be automatically determined. For example, EGM signals may be stored for a period of time beginning a predetermined number of beats preceding the beginning of an arrhythmia episode and continuing for a predetermined number of beats following an ending of the arrhythmia episode. It is recognized that the storage of the EGM signals may be managed in various manners. Thereafter, flow moves to 1104.

At 1104, the one or more processors initiate a P-wave under-sensing discriminator. The P-wave undersensing discriminator, among other things, implements a P-wave detection and confirmation process in accordance with embodiments herein. For example, the P-wave undersensing discriminator may analyze the stored segment of EGM signals, among other things, by analyzing the beats within the segment of EGM signals for candidate P waves. The P-wave undersensing discriminator then implements the methods and systems herein to detect and compare alignment indicators and amplitude dependence indicators with corresponding criteria to declare candidate P waves valid actual P waves or false P waves. The remaining operations of FIG. 11A further summarize one manner in which the segment of EGM signals may be analyzed based on candidate and actual P waves. The P-wave under sensing discriminator at operation 1104-1110 may be implemented in real time within an IMD while collecting real-time CA signals and performing real time arrhythmia detection. Additionally or alternatively, the P-wave under sensing discriminator at operations 1104-1110 may be implemented at a later point in time following one or more candidate arrhythmia episodes. For example, the stored segments of EGM signals and the determinations of arrhythmia episodes may be downloaded from the IMD to an external device and/or optionally to a remote server. FIGS. 9 and 10 illustrate nonlimiting examples of configurations of local and remote external devices/servers that may communicate with an implantable device to perform all or portions of the P-wave detection and discrimination processes described herein, as well as numerous other operations. The local external device and/or remote server (or any other non-implantable computing device) may then implement the P-wave under sensing discriminator by performing the operations described herein in connection with FIGS. 1-10

At 1106, the one or more processors (IMD, local external device, remote server, etc.) analyze the segment of stored EGM signals, associated with the candidate arrhythmia episode, to search for the presence of consistent P waves in search windows preceding the corresponding R waves. As a nonlimiting example, the EGM signals for a 30 second period of time prior to declaration of the candidate arrhythmia episode may be analyzed for P waves. One or more of the P-wave detection processes herein are applied across the segment of EGM signals, to detect candidate P waves and then analyze the alignment and AD indicators relative to first and second criteria to validate or reject the candidate P waves. The actual P-waves are assigned corresponding P-wave markers. At 1106, the one or more processors determine whether consistent P waves are detected across the beats within the segment of EGM signals. The determination for what constitutes "consistent" P waves may vary. For example, the process may determine that consistent P waves are present when at least 80% of the beats exhibit an actual P-wave. Additionally or alternatively, the process may declare that consistent P waves are present when actual P waves are detected in X out of Y beats (e.g., 3 out of 4, 7 out of 8, etc.). When consistent P waves are not found, flow moves to 1108. At 1108, the one or more processors validates the arrhythmia episode, namely the one or more processors interpret the lack of P waves as an indication that the arrhythmia detection algorithm correctly identified an arrhythmia episode. Alternatively, if consistent P waves are found at 1106, flow moves to 1110. At 1110, the one or more processors reject the arrhythmia episode as false, namely the one or more processors determine that the arrhythmia detection algorithm has under sensed P waves and rejects.

In accordance with new and unique aspects herein, methods and systems are provided that collect CA signals, identify variability in RR intervals within a series of beats in the CA signals, declare an arrhythmia episode based on the variability in the RR intervals, store a segment of the CA signals for a series of beats in connection with the arrhythmia episode and implement a confirmation/rejection process based on the determination of whether P waves have been under sensed. The confirmation/rejection process implements the P-wave detection processes and systems described herein. By way of example, methods and systems iteratively implementing the applying, calculating, analyzing, comparing, and designating operations of FIGS. 3A and/or 3B to determine whether actual P waves occur consistently throughout the series of beats; and the validate or reject the arrhythmia episode based on the determination of whether the actual P waves occur consistently throughout the series of beats.

Among other things, the P-wave detection comprises obtaining far field cardiac activity (CA) signals for a series of beats; applying a P-wave template to at least one sub-segment of the CA signals to obtain an alignment indicator; calculating an amplitude dependence (AD) indicator based at least in part on the P-wave template and the at least one sub-segment; analyzing the alignment indicator based on a first criteria; comparing the AD indicator with a second criteria; designating a candidate P-wave to be an actual P-wave based on the analyzing and comparing; and recording results of the designating (e.g., FIGS. 3A and 3B).

Additionally or alternatively, the P-wave detection process and system further comprises: identifying an R-wave COI from a beat in the series of beats; defining the P-wave search window to overlay the sub-segment of the CA signals at a predetermined time prior to the R-wave COI for the beat; collecting the subsegment of the CA signals overlaid by the P-wave search window; repeating the identifying, defining and collecting to obtain on ensemble of subsegments for the series of beats, combining the ensemble of subsegments to form an ensemble average of the CA signals within the P-wave search window for the series of beats; and calculating a correlation of the ensemble average with the P-wave template to obtain the alignment indicator (e.g., FIG. 3B).

Additionally or alternatively, the P-wave detection process and system performs the applying operation by applying the P-wave template to sub-segments of the CA signals along a P-wave search window to obtain, as the alignment indicator (e.g., FIG. 3A), a temporal alignment (TA) indicator across the P-wave search window, and performs the analyzing operation by analyzing the TA indicator based on the first criteria to identify the candidate P-wave (e.g., FIG. 3A).

Figure 11B:
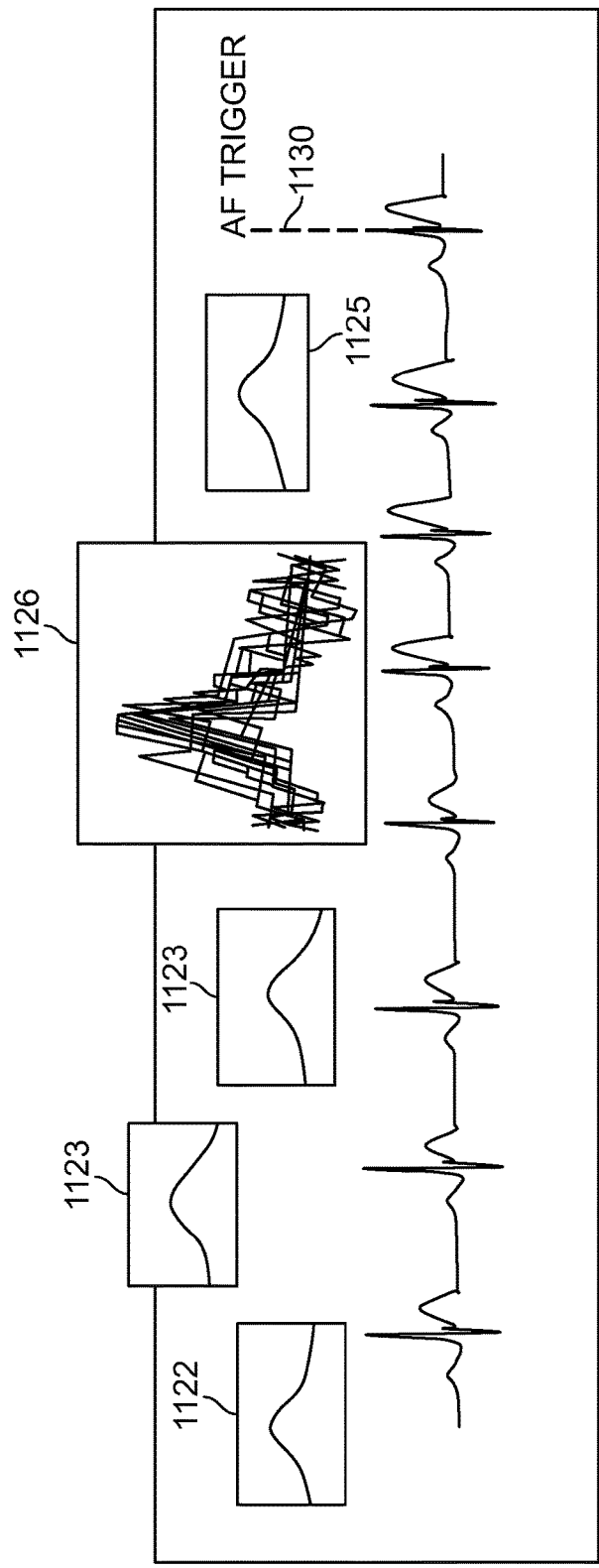
FIG. 11B illustrates an example for consistent P waves analyzed in accordance with embodiments herein.

FIG. 11B illustrates an example for consistent P waves analyzed in accordance with embodiments herein. A window 1120 of CA signals preceding an AF trigger 1130 is illustrated, from which candidate P-wave segments 1122-1125 are identified. The candidate P-wave segments 1122-1125 are overlapped to form a candidate P-wave ensemble 1126. The candidate P-wave ensemble is then analyzed in accordance with embodiments herein. It is recognized that the illustration at 1126 merely represents examples of various candidate P waves that may be then combined to form an ensemble through various mathematical functions.

Figure 11C:
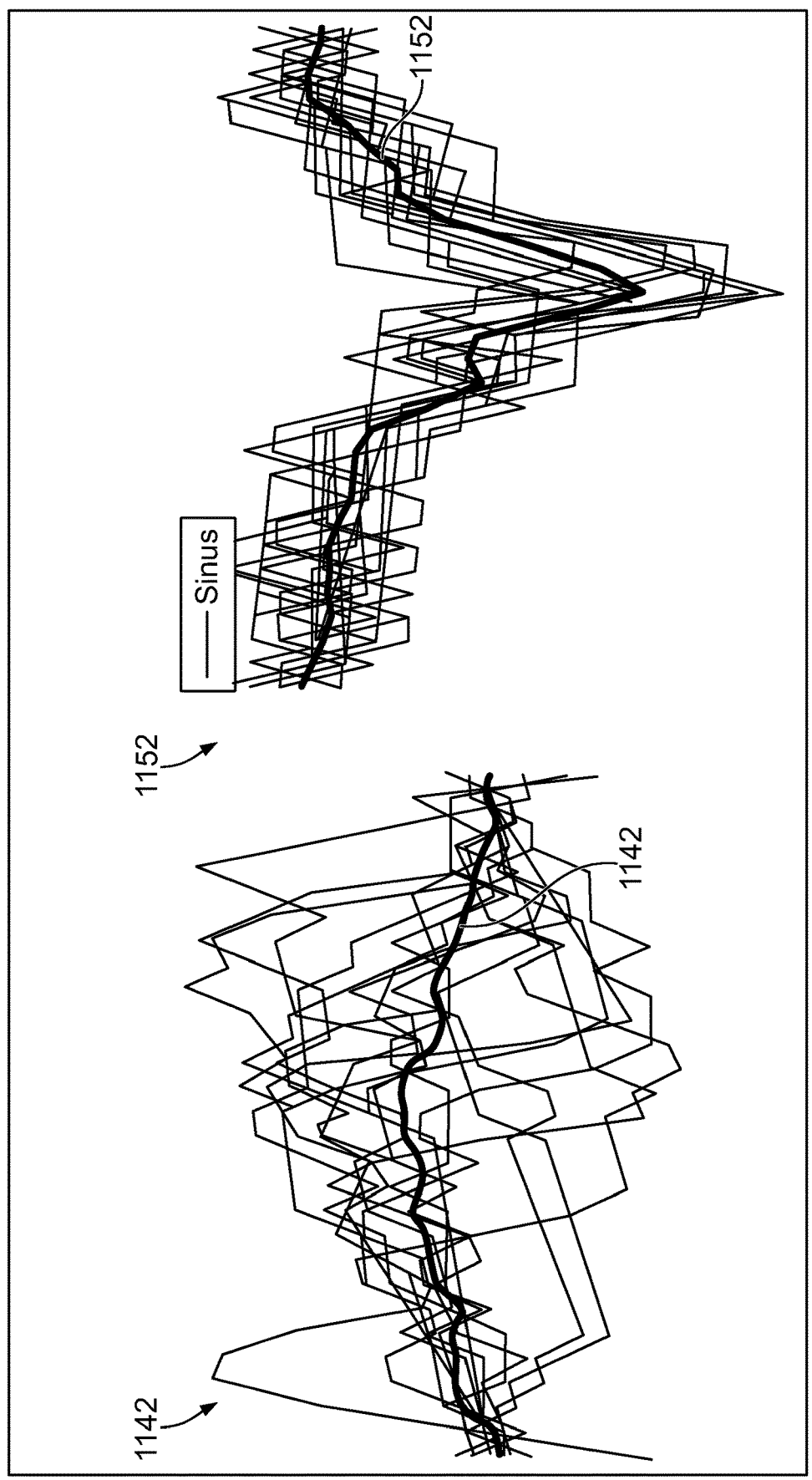
FIG. 11C illustrates alternative examples of groups of candidate P waves that may be combined.

FIG. 11C illustrates alternative examples of groups of candidate P waves that may be combined. In panel 1140, the candidate P waves, when combined, form an ensemble 1142 that would not satisfy the first and/or second criteria for a TA indicator and/or an AD indicator in accordance with embodiments herein. Consequently, the ensemble 1142 would be classified to not represent a P-wave ensemble and thus the AF episode would be validated. In panel 1150, the candidate P waves, when combined, form an ensemble 1152 that would satisfy the first and second criteria for the TA indicator and the AD indicator in accordance with embodiments herein. Consequently, the ensemble 1152 would be classified to represent a P-wave ensemble and thus the AF episode would be declared invalid.

Additionally or alternatively, the AF detection algorithm may discriminate AF based on a variability in the RR interval. When an AF detection algorithm exhibits an excessive amount of variability in the RR interval, the P-wave detection processes herein may be implemented in connection there with to determine whether a P-wave occurred preceding each of the R waves used to determine the RR interval. When P waves do not precede the R waves, this may be taken as a further indication that the AF detection algorithm has incorrectly identified in R-wave (given that the R-wave is not preceded by a P wave).

The P-wave detection algorithms herein may be utilized in connection with other processes (not related to AF) for monitoring and detecting various physiologic states and delivering therapy. As one nonlimiting example, the P-wave detection processes herein may be utilized in combination with assessing the left atrial pressure (LAP), such as described in U.S. Pat. No. 8,600,487, titled "SYSTEM AND METHOD FOR EXPLOITING ATRIAL ELECTROCARDIAC PARAMETERS IN ASSESSING LEFT ATRIAL PRESSURE USING AN IMPLANTABLE MEDICAL DEVICE", issuing Dec. 3, 2013, the complete subject matter of which is expressly incorporated by reference herein in its entirety. For example, the P-wave detection processes herein may be utilized to detect a peak of the P-wave, and in connection there with calculating an intra-atrial conduction (IACD) delay and P-wave duration. In accordance with embodiments in the '487 patent, the IMD then tracks changes, if any, in the intra-atrial conduction delay, P-wave duration, and other parameters in connection with values measured for left atrial pressure. As nonlimiting examples, the P-wave detection processes herein may be used to detect atrial parameters, such as the IACD delay and P-wave duration, in connection with FIG. 2 (operation 102), FIG. 3A (operation 152), FIG. 4, (operation 202) FIG. 5 (operation 256), and FIG. 6 in the '487 patent.

Additionally or alternatively, the P-wave detection processes described herein may be implement it in connection with reducing false bradycardia detection. For example, the P-wave detection processes herein may be utilized to adjust sensing threshold's to be applied in connection with each episode to provide a more customized approach.

Additionally or alternatively, the P-wave detection processes described herein may be implemented in connection with reducing false positive detection. While false positive actions are often frequently due to under sensed R waves, the P-wave detected in connection here with may be utilized to adjust sensing thresholds to provide a more customized approach. For example, when a positive is detected, a window may be defined that precedes the pause. The P-wave detection process herein may be implemented across the CA signals within the window to search for P waves that may be then utilized to better determine whether a pause has in fact occurred.

Additionally or alternatively, the P-wave detection processes described herein may be implement in connection with discriminating loss of contact, such as when an electrode on ICM loses contact with the surrounding tissue. False pause detections due to loss of contact also exhibit a small characteristic noise signal. However, at times it may be difficult to distinguish between a noise signal and a P-wave. The P-wave templates described herein may be applied across the window that includes the potential noise signal. When the criteria herein indicate that the window includes an actual or true P-wave, the process may determine that there is no loss of contact. Alternatively, when the criteria herein indicate that the window does not include an actual or true P-wave, the processes herein may be utilized to verify that the window does not in fact only include noise and therefore provide a further confirmation that loss of contact has occurred.

CLOSING

The various methods as illustrated in the Figures and described herein represent exemplary embodiments of methods. The methods may be implemented in software, hardware, or a combination thereof. In various of the methods, the order of the steps may be changed, and various elements may be added, reordered, combined, omitted, modified, etc. Various of the steps may be performed automatically (e.g., without being directly prompted by user input) and/or programmatically (e.g., according to program instructions).

Various modifications and changes may be made as would be obvious to a person skilled in the art having the benefit of this disclosure. It is intended to embrace all such modifications and changes and, accordingly, the above description is to be regarded in an illustrative rather than a restrictive sense.

Various embodiments of the present disclosure utilize at least one network that would be familiar to those skilled in the art for supporting communications using any of a variety of commercially-available protocols, such as Transmission Control Protocol/Internet Protocol ("TCP/IP"), User Datagram Protocol ("UDP"), protocols operating in various layers of the Open System Interconnection ("OSI") model, File Transfer Protocol ("FTP"), Universal Plug and Play ("UpnP"), Network File System ("NFS"), Common Internet File System ("CIFS") and AppleTalk. The network can be, for example, a local area network, a wide-area network, a virtual private network, the Internet, an intranet, an extranet, a public switched telephone network, an infrared network, a wireless network, a satellite network and any combination thereof.

In embodiments utilizing a web server, the web server can run any of a variety of server or mid-tier applications, including Hypertext Transfer Protocol ("HTTP") servers, FTP servers, Common Gateway Interface ("CGI") servers, data servers, Java servers, Apache servers and business application servers. The server(s) also may be capable of executing programs or scripts in response to requests from user devices, such as by executing one or more web applications that may be implemented as one or more scripts or programs written in any programming language, such as Java®, C, C# or C++, or any scripting language, such as Ruby, PHP, Perl, Python or TCL, as well as combinations thereof. The server(s) may also include database servers, including without limitation those commercially available from Oracle®, Microsoft®, Sybase® and IBM® as well as open-source servers such as MySQL, Postgres, SQLite, MongoDB, and any other server capable of storing, retrieving and accessing structured or unstructured data. Database servers may include table-based servers, document-based servers, unstructured servers, relational servers, non-relational servers or combinations of these and/or other database servers.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

All references, including publications, patent applications and patents, cited herein are hereby incorporated by reference to the same extent as if each reference were individually and specifically indicated to be incorporated by reference and were set forth in its entirety herein.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and physical characteristics described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

What is claimed is:

1. A system for detecting P-waves in cardiac activity, comprising:
    memory to store specific executable instructions;
    one or more processors configured to execute the specific executable instructions for:
    obtaining far field cardiac activity (CA) signals for a series of beats;
    applying a P-wave template to at least one sub-segment of the CA signals to obtain an alignment indicator;
    calculating an amplitude dependence (AD) indicator based at least in part on the P-wave template and the at least one sub-segment;
    analyzing the alignment indicator based on a first criteria;
    comparing the AD indicator with a second criteria;
    designating a candidate P-wave to be an actual P-wave based on the analyzing and comparing; and
    recording results of the designating.

2. The system of claim 1, wherein the one or more processors further configured to execute the specific executable instructions for:
    identifying an R-wave COI from a beat in the series of beats;
    defining the P-wave search window to overlay the sub-segment of the CA signals at a predetermined time prior to the R-wave COI for the beat;
    collecting the subsegment of the CA signals overlaid by the P-wave search window;
    repeating the identifying, defining and collecting to obtain on ensemble of subsegments for the series of beats, combining the ensemble of subsegments to form an ensemble average of the CA signals within the P-wave search window for the series of beats; and
    calculating a correlation of the ensemble average with the P-wave template to obtain the alignment indicator.

3. The system of claim 1, wherein the applying by the one or more processors further comprises applying the P-wave template to sub-segments of the CA signals along a P-wave search window to obtain, as the alignment indicator, a temporal alignment (TA) indicator across the P-wave search window, and wherein the analyzing by the one or more processors further comprises analyzing the TA indicator based on the first criteria to identify the candidate P-wave.

4. The system of claim 3, wherein the TA indicator represents a measure of how changes in the P-wave template are associated with changes in the corresponding subsegments of the CA signals and wherein the first criteria corresponds to a maximum for the TA indicator over the P-wave search window, the candidate P-wave corresponding to the subsegment of the CA signal for which the corresponding TA indicator has the maximum.

5. The system of claim 3, wherein the one or more processors are configured to iteratively correlate the P-wave template to the sub-segments of the CA signals along the P-wave search window to obtain a correlation function across the P-wave search window as the temporal alignment indicator.

6. The system of claim 5, wherein the one or more processors are configured to analyze the temporal alignment indicator by identify a peak in the correlation function and identify the candidate P-wave based on the peak in the correlation function.

7. The system of claim 5, wherein the one or more processors are configured to calculate a covariance function based on the correlation function, the covariance function representing the AD indicator.

8. The system of claim 7, wherein the second criteria represents a tolerance range that is defined based on a peak of the P-wave template, and wherein the one or more processors are configured to determine whether the covariance function is within the tolerance range.

9. The system of claim 1, wherein the one or more processors are configured to apply the P-wave template to the segments of an ensemble of CA signals collected over multiple beats.

10. The system of claim 1, wherein the one or more processors are configured to calculate a plurality of P-wave templates associated with different postures and utilize a select one of the P-wave templates based on a current posture of the patient when the CA signals are collected.

11. A computer implemented method, comprising:
under control of one or more processors configured with specific executable instructions,
obtaining far field cardiac activity (CA) signals for a series of beats;
applying a P-wave template to at least one sub-segment of the CA signals to obtain an alignment indicator;
calculating an amplitude dependence (AD) indicator based at least in part on the P-wave template and the at least one sub-segment;
analyzing the alignment indicator based on a first criteria;
comparing the AD indicator with a second criteria;
designating a candidate P-wave to be an actual P-wave based on the analyzing and comparing; and
recording results of the designating.

12. The method of claim 11, further comprising:
identifying an R-wave COI from a beat in the series of beats;
defining the P-wave search window to overlay the sub-segment of the CA signals at a predetermined time prior to the R-wave COI for the beat;
collecting the subsegment of the CA signals overlaid by the P-wave search window;
repeating the identifying, defining and collecting to obtain on ensemble of subsegments for the series of beats, combining the ensemble of subsegments to form an ensemble average of the CA signals within the P-wave search window for the series of beats; and
calculating a correlation of the ensemble average with the P-wave template to obtain the alignment indicator.

13. The method of claim 11, wherein the applying further comprises applying the P-wave template to sub-segments of the CA signals along a P-wave search window to obtain, as the alignment indicator, a temporal alignment (TA) indicator across the P-wave search window, and wherein the analyzing further comprises analyzing the TA indicator based on the first criteria to identify the candidate P-wave.

14. The method of claim 13, wherein applying includes iteratively correlating the P-wave template to the sub-segments of the CA signals along the P-wave search window to obtain a correlation function across the P-wave search window as the temporal alignment indicator.

15. The method of claim 14, wherein the analyzing the temporal alignment indicator based on the first criteria includes identifying a peak in the correlation function and identifying the candidate P-wave based on the peak in the correlation function.

16. The method of claim 11, wherein the one or more processors are configured to at least one of:
i) perform the applying, calculating, analyzing and comparing in a parallel manner, or
ii) perform the applying, calculating, analyzing and comparing in a serial manner.

17. The method of claim 11, wherein the CA signals represent intracardiac electrograms (IEGM), the method further comprising calculating the P-wave template by:
displaying on a graphical user interface (GUI) IEGM signals and surface electrocardiogram (EKG) signals;
receiving a user input from the GUI an input designating at least one of:
1) P-waves on the IEGM signals,
2) P-waves on surface EKG signals and P waves on the IEGM signals, or
3) P-waves on the surface EKG signals;
the user input designating select points corresponding to the P-waves; and
identifying the segment of the CA signals that includes the corresponding P-waves.

18. The method of claim 17, further comprising repeating the displaying, receiving and identifying to calculate a plurality of P-wave templates associated with different postures and utilizing a select one of the P-wave templates based on a current posture of the patient when the CA signals are collected.

19. The method of claim 18, further comprising calculating separate P-wave templates corresponding to a patient standing, the patient sitting, the patient lying on his/her back, and the patient lying on each side.

20. The method of claim 11, wherein the obtaining the CA signals further comprises collecting the CA signals in real time by an implantable medical device in connection with an arrhythmia detection process, the arrhythmia detection processes comprising:
identifying variability in RR intervals within the series of beats in the CA signals;
declaring an arrhythmia episode based on variability in the RR intervals;
storing a segment of the CA signals for the series of beats in connection with the arrhythmia episode;
iteratively implementing the applying, calculating, analyzing, comparing, and designating to determine whether actual P waves occur consistently throughout the series of beats; and
validating or rejecting the arrhythmia episode based on the determination of whether the actual P waves occur consistently throughout the series of beats.

* * * * *